(12) United States Patent
Batchelder et al.

(10) Patent No.: US 12,708,385 B2
(45) **Date of Patent: *Aug. 18, 2026**

(54) SYSTEMS, DEVICES AND METHODS FOR GENERATING PATTERNS OF VOLTAGE PULSES AND ELECTRICAL ARCS BETWEEN SPACED-APART ELECTRODE PAIRS IN INTRAVASCULAR LITHOTRIPSY

(71) Applicant: Cardiovascular Systems, Inc., Santa Clara, CA (US)

(72) Inventors: J. Samuel Batchelder, Woodinville, WA (US); John R. Ballard, Waconia, MN (US); Robert D'Agostino, Minneapolis, MN (US); Michael P. Brenzel, St. Paul, MN (US); Jason W. Staab, Apple Valley, MN (US)

(73) Assignee: Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/400,606

(22) Filed: Nov. 25, 2025

(65) Prior Publication Data

US 2026/0157765 A1 Jun. 11, 2026

Related U.S. Application Data

(63) Continuation of application No. 17/449,883, filed on Oct. 4, 2021.

(Continued)

(51) Int. Cl.
*A61B 17/22* (2006.01)
*A61M 25/10* (2013.01)

(52) U.S. Cl.
CPC .................. *A61B 17/22022* (2013.01); *A61B 2017/22062* (2013.01); *A61M 25/104* (2013.01)

(58) Field of Classification Search
CPC A61B 2017/22098; A61B 2017/22025; A61B 2017/2202; A61B 2017/00557; A61B 17/225; A61M 25/104
See application file for complete search history.

(56) References Cited

U.S. PATENT DOCUMENTS 2,916,647 A 12/1959 George
3,412,288 A 11/1968 Ostrander (Continued)

FOREIGN PATENT DOCUMENTS

AT E482647 T1 10/2010
AU 22933/88 A 4/1989

(Continued)

OTHER PUBLICATIONS

Ali, Z. "The Sound Science Behind Shockwave IVL's Mechanism of Action", Transcatheter Cardiovascular Therapeutics, Peripheral IVL Speaker Deck, believed to be presented Oct. 29, 2024.

(Continued)

*Primary Examiner* — Anh T Dang
(74) *Attorney, Agent, or Firm* — Workman Nydegger

(57) ABSTRACT

A pressure wave generating catheter system includes a catheter and a plurality of electrodes disposed within in the catheter. A fluid-fillable balloon encloses the plurality of electrodes. A pulse generator is coupled in electrical communication with the plurality of electrodes in the catheter. The pulse generator is configured to for a given cycle, cause a first voltage pulse to be applied to at least a portion of the plurality of electrodes in the catheter, after which a second voltage pulse is applied to at least a portion of the plurality of electrodes in the catheter, the first voltage pulse causing an initial pressure wave, and wherein the second voltage pulse occurs prior to the initial pressure wave resulting from the first voltage pulse dissipating.

18 Claims, 7 Drawing Sheets

Related U.S. Application Data

(60) Provisional application No. 63/229,737, filed on Aug. 5, 2021.

(56) References Cited

U.S. PATENT DOCUMENTS 3,413,976 A 12/1968 Leo
3,524,101 A 8/1970 Spartacus
3,583,766 A 6/1971 Padberg, Jr.
3,735,764 A 5/1973 Balev et al.
3,785,382 A 1/1974 Schmidt et al.
3,902,499 A 9/1975 Shene
3,942,531 A 3/1976 Hoff et al.
4,027,674 A 6/1977 Tessler et al.
4,030,505 A 6/1977 Tessler
4,191,189 A 3/1980 Barkan
4,445,509 A 5/1984 Auth
4,446,867 A 5/1984 Leveen et al.
4,587,975 A 5/1986 Salo et al.
4,608,983 A 9/1986 Mueller et al.
4,643,186 A 2/1987 Rosen et al.
4,662,126 A 5/1987 Malcolm
4,662,375 A 5/1987 Hepp et al.
4,671,254 A 6/1987 Fair
4,685,458 A 8/1987 Leckrone
4,697,588 A 10/1987 Reichenberger
4,702,248 A 10/1987 Mestas et al.
4,715,375 A 12/1987 Nowacki et al.
4,715,376 A 12/1987 Nowacki et al.
4,741,405 A 5/1988 Moeny et al.
4,766,608 A 8/1988 Cusick et al.
4,781,677 A 11/1988 Wilcox
4,793,329 A 12/1988 Mahler et al.
4,799,482 A 1/1989 Takayama
4,809,682 A 3/1989 Forssmann et al.
4,813,934 A 3/1989 Engelson et al.
4,878,495 A 11/1989 Grayzel
4,890,603 A 1/1990 Filler
4,900,303 A 2/1990 Lemelson
4,901,709 A 2/1990 Rattner
4,905,673 A 3/1990 Pimiskern
4,905,675 A 3/1990 Oppelt
4,909,252 A 3/1990 Goldberger
4,915,094 A 4/1990 Lacruche et al.
4,930,496 A 6/1990 Bosley, Jr.
4,936,281 A 6/1990 Stasz
4,955,143 A 9/1990 Hagelauer
4,955,377 A 9/1990 Lennox et al.
4,955,385 A 9/1990 Kvalo et al.
4,961,738 A 10/1990 Mackin
4,962,753 A 10/1990 Cathignol et al.
4,966,132 A 10/1990 Nowacki et al.
4,968,314 A 11/1990 Michaels
4,990,134 A 2/1991 Auth
4,994,032 A 2/1991 Sugiyama et al.
4,998,932 A 3/1991 Rosen et al.
5,002,085 A 3/1991 Fitzgerald
5,009,232 A 4/1991 Hassler et al.
5,040,548 A 8/1991 Yock
5,046,503 A 9/1991 Schneiderman
5,057,103 A 10/1991 Davis
5,057,106 A 10/1991 Kasevich et al.
5,057,107 A 10/1991 Parins et al.
5,061,240 A 10/1991 Cherian
5,072,723 A 12/1991 Viebach
5,078,717 A 1/1992 Parins et al.
5,102,402 A 4/1992 Dror et al.
5,103,804 A 4/1992 Abele et al.
5,116,227 A 5/1992 Levy
5,146,912 A 9/1992 Eizenhoefer
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Mueller et al.
5,211,683 A 5/1993 Maginot
5,231,976 A 8/1993 Wiksell
5,233,980 A 8/1993 Mestas et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,304,220 A 4/1994 Maginot
5,308,354 A 5/1994 Zacca et al.
5,320,634 A 6/1994 Vigil et al.
5,321,715 A 6/1994 Trost
5,324,255 A 6/1994 Passafaro et al.
5,336,234 A 8/1994 Vigil et al.
5,358,487 A 10/1994 Miller
5,362,309 A 11/1994 Carter
5,364,393 A 11/1994 Auth et al.
5,366,443 A 11/1994 Eggers et al.
5,368,591 A 11/1994 Lennox et al.
5,395,335 A 3/1995 Jang
5,395,361 A 3/1995 Fox et al.
5,411,016 A 5/1995 Kume et al.
5,417,208 A 5/1995 Winkler
5,425,735 A 6/1995 Rosen et al.
5,429,617 A 7/1995 Hammersmark et al.
5,431,663 A 7/1995 Carter
5,433,731 A 7/1995 Hoegnelid et al.
5,454,809 A 10/1995 Janssen
5,456,712 A 10/1995 Maginot
5,458,652 A 10/1995 Uebelacker
5,470,352 A 11/1995 Rappaport
5,472,406 A 12/1995 Torre et al.
5,474,080 A 12/1995 Hughes
5,520,645 A 5/1996 Imran et al.
5,571,167 A 11/1996 Maginot
5,582,578 A 12/1996 Zhong et al.
5,584,843 A 12/1996 Wulfman et al.
5,603,731 A 2/1997 Whitney
5,609,606 A 3/1997 O'Boyle
5,611,807 A 3/1997 O'Boyle
5,662,590 A 9/1997 Torre et al.
5,681,336 A 10/1997 Clement et al.
5,709,676 A 1/1998 Alt
5,741,246 A 4/1998 Prescott
5,749,375 A 5/1998 Maginot
5,766,152 A 6/1998 Morley et al.
5,836,874 A 11/1998 Swanson et al.
5,841,737 A 11/1998 Schaefer
5,846,218 A 12/1998 Brisken et al.
5,891,089 A 4/1999 Katz et al.
5,893,840 A 4/1999 Hull et al.
5,931,805 A 8/1999 Brisken
5,967,984 A 10/1999 Chu et al.
5,979,455 A 11/1999 Maginot
5,995,871 A 11/1999 Knisley
6,001,069 A 12/1999 Tachibana et al.
6,007,530 A 12/1999 Doernhoefer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster, Jr.
6,113,560 A 9/2000 Simnacher
6,123,718 A 9/2000 Tu et al.
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,287,331 B1 9/2001 Heath
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,375,651 B2 4/2002 Grasso et al.

(56) References Cited

U.S. PATENT DOCUMENTS 6,390,995 B1 5/2002 Ogden et al.
6,398,792 B1 6/2002 O'Connor
6,401,721 B1 6/2002 Maginot
6,406,486 B1 6/2002 Torre et al.
6,440,124 B1 8/2002 Esch et al.
6,456,888 B1 9/2002 Skinner et al.
6,464,660 B2 10/2002 Brisken et al.
6,494,890 B1 12/2002 Shturman et al.
6,500,174 B1 12/2002 Maguire et al.
6,514,203 B2 2/2003 Bukshpan
6,524,251 B2 2/2003 Rabiner et al.
6,589,253 B1 7/2003 Cornish et al.
6,599,313 B1 7/2003 Maginot
6,607,003 B1 8/2003 Wilson
6,635,054 B2 10/2003 Fjield et al.
6,638,246 B1 10/2003 Naimark et al.
6,652,547 B2 11/2003 Rabiner et al.
6,666,828 B2 12/2003 Greco et al.
6,666,834 B2 12/2003 Restle et al.
6,669,655 B1 12/2003 Acker et al.
6,689,089 B1 2/2004 Tiedtke et al.
6,726,681 B2 4/2004 Grasso et al.
6,736,784 B1 5/2004 Menne et al.
6,736,811 B2 5/2004 Panescu et al.
6,740,081 B2 5/2004 Hilal
6,755,821 B1 6/2004 Fry
6,758,847 B2 7/2004 Maguire
6,761,708 B1 7/2004 Chiu et al.
6,800,080 B1 10/2004 Bates
6,939,320 B2 9/2005 Lennox
6,954,977 B2 10/2005 Maguire et al.
6,989,009 B2 1/2006 Lafontaine
7,033,383 B1 4/2006 Maginot
7,066,904 B2 6/2006 Rosenthal et al.
7,087,061 B2 8/2006 Chernenko et al.
7,104,983 B2 9/2006 Grasso et al.
7,153,315 B2 12/2006 Miller
7,175,605 B2 2/2007 Tiedtke et al.
7,241,295 B2 7/2007 Maguire
7,247,269 B2 7/2007 Keidar
7,309,324 B2 12/2007 Hayes et al.
7,379,767 B2 5/2008 Rea
7,389,148 B1 6/2008 Morgan
7,390,308 B2 6/2008 Schultheiss
7,410,486 B2 8/2008 Fuimaono et al.
7,505,812 B1 3/2009 Eggers et al.
7,540,846 B2 6/2009 Harhen et al.
7,569,032 B2 8/2009 Naimark et al.
7,597,697 B1 10/2009 Maginot
7,628,785 B2 12/2009 Hadjicostis et al.
7,651,492 B2 1/2010 Wham
7,720,521 B2 5/2010 Chang et al.
7,736,362 B2 6/2010 Eberl et al.
7,744,595 B2 6/2010 Truckai et al.
7,744,620 B2 6/2010 Pedersen et al.
7,753,946 B2 7/2010 Maginot
7,754,047 B2 7/2010 Kelley
7,829,029 B2 11/2010 Zumeris et al.
7,837,672 B2 11/2010 Intoccia
7,850,685 B2 12/2010 Kunis et al.
7,853,332 B2 12/2010 Olsen et al.
7,855,904 B2 12/2010 Kirbie et al.
7,873,404 B1 1/2011 Patton
7,914,525 B2 3/2011 Abboud et al.
7,920,921 B2 4/2011 Syed et al.
7,942,850 B2 5/2011 Levit et al.
7,951,111 B2 5/2011 Drasler et al.
7,959,602 B2 6/2011 Tiedtke et al.
8,025,661 B2 9/2011 Arnold et al.
8,133,199 B2 3/2012 Weber et al.
8,162,859 B2 4/2012 Schultheiss et al.
8,177,801 B2 5/2012 Kallok et al.
8,182,530 B2 5/2012 Huber
8,197,463 B2 6/2012 Intoccia
8,241,272 B2 8/2012 Arnold et al.
8,277,444 B2 10/2012 Arnold et al.
8,333,763 B2 12/2012 Truckai et al.
8,343,170 B2 1/2013 Massicotte et al.
8,353,923 B2 1/2013 Shturman
8,366,705 B2 2/2013 Arnold et al.
8,382,771 B2 2/2013 Gellman et al.
8,444,639 B2 5/2013 Arnold et al.
8,518,038 B2 8/2013 Swanson
8,529,581 B2 9/2013 Massicotte et al.
8,556,813 B2 10/2013 Cioanta et al.
8,556,890 B2 10/2013 Wham
8,574,247 B2 11/2013 Adams et al.
8,632,461 B2 1/2014 Glossop
8,685,201 B2 4/2014 O'Rourke et al.
8,709,075 B2 4/2014 Adams et al.
8,728,091 B2 5/2014 Hakala et al.
8,747,416 B2 6/2014 Hakala et al.
8,790,359 B2 7/2014 Rabiner et al.
8,805,466 B2 8/2014 Salahieh et al.
8,888,788 B2 11/2014 Hakala et al.
8,897,869 B2 11/2014 Kassab
8,900,166 B2 12/2014 Spector
8,900,264 B2 12/2014 Drasler et al.
8,926,630 B2 1/2015 Diamant et al.
8,956,371 B2 2/2015 Hawkins et al.
8,956,374 B2 2/2015 Hawkins et al.
9,005,198 B2 4/2015 Long et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.
9,044,619 B2 6/2015 Hawkins et al.
9,072,534 B2 7/2015 Adams et al.
9,119,624 B2 9/2015 Wham
9,138,249 B2 9/2015 Adams et al.
9,161,768 B2 10/2015 Cioanta et al.
9,180,280 B2 11/2015 Hawkins et al.
9,192,772 B1 11/2015 Tsukamoto et al.
9,198,825 B2 12/2015 Katragadda et al.
9,220,521 B2 12/2015 Hawkins et al.
9,277,955 B2 3/2016 Herscher et al.
9,289,258 B2 3/2016 Cohen
9,333,000 B2 5/2016 Hakala et al.
9,375,533 B2 6/2016 Ducharme et al.
9,421,025 B2 8/2016 Hawkins et al.
9,431,428 B2 8/2016 Yamazaki
9,433,428 B2 9/2016 Hakala et al.
9,504,807 B2 11/2016 Drasler et al.
9,522,012 B2 12/2016 Adams
9,579,114 B2 2/2017 Mantell et al.
9,610,006 B2 4/2017 Salahieh et al.
9,636,124 B2 5/2017 Mantell
9,642,673 B2 5/2017 Adams et al.
9,717,513 B2 8/2017 Golan
9,730,715 B2 8/2017 Adams
9,743,980 B2 8/2017 Diamant et al.
9,757,194 B2 9/2017 Werneth et al.
9,763,624 B2 9/2017 Stanislaus et al.
9,808,167 B2 11/2017 Kassab
9,814,476 B2 11/2017 Adams et al.
9,833,373 B2 12/2017 Brouillette et al.
9,861,377 B2 1/2018 Mantell
9,867,629 B2 1/2018 Hawkins
9,913,594 B2 3/2018 Li et al.
9,974,607 B2 5/2018 Stone et al.
9,993,292 B2 6/2018 Adams et al.
10,010,666 B2 7/2018 Rubinsky et al.
10,039,561 B2 8/2018 Adams et al.
10,058,340 B2 8/2018 Cioanta et al.
10,118,015 B2 11/2018 De et al.
10,149,690 B2 12/2018 Hawkins et al.
10,154,799 B2 12/2018 Van et al.
10,159,505 B2 12/2018 Hakala et al.
10,194,930 B2 2/2019 Du
10,206,698 B2 2/2019 Hakala et al.
10,219,720 B2 3/2019 Kassab
10,226,265 B2 3/2019 Ku et al.
10,238,405 B2 3/2019 Cioanta et al.
10,238,408 B2 3/2019 Zhong et al.

(56) References Cited

U.S. PATENT DOCUMENTS 10,357,264 B2 7/2019 Kat-Kuoy
10,364,981 B2 7/2019 Wang et al.
10,426,500 B2 10/2019 Lipowski et al.
10,478,202 B2 11/2019 Adams et al.
10,500,128 B2 12/2019 Engles et al.
10,517,620 B2 12/2019 Adams
10,517,621 B1 12/2019 Hakala et al.
10,555,744 B2 2/2020 Nguyen et al.
10,603,058 B2 3/2020 Mantell
10,639,051 B2 5/2020 Cioanta et al.
10,646,240 B2 5/2020 Betelia et al.
10,661,034 B2 5/2020 Mantell et al.
10,668,208 B2 6/2020 Rubinsky et al.
10,682,178 B2 6/2020 Adams et al.
10,702,293 B2 7/2020 Adams et al.
10,709,462 B2 7/2020 Nguyen et al.
10,751,000 B2 8/2020 Hacker
10,756,440 B2 8/2020 Asagi et al.
10,765,440 B2 9/2020 Tozzi
10,786,267 B2 9/2020 Wasdyke et al.
10,806,504 B2 10/2020 Hubelbank
10,842,567 B2 11/2020 Grace et al.
10,849,637 B1 12/2020 Mantell
10,849,879 B2 12/2020 Seward
10,850,078 B2 12/2020 Grace et al.
10,856,893 B2 12/2020 Eggert et al.
10,888,373 B2 1/2021 Koblish et al.
10,893,903 B2 1/2021 Koblish et al.
10,898,213 B2 1/2021 Grace et al.
10,959,743 B2 3/2021 Adams et al.
10,966,737 B2 4/2021 Nguyen
10,973,538 B2 4/2021 Hakala et al.
11,000,299 B2 5/2021 Hawkins et al.
11,020,135 B1 6/2021 Hawkins
11,026,707 B2 6/2021 Ku et al.
11,058,492 B2 7/2021 Grace et al.
11,076,874 B2 8/2021 Hakala et al.
11,103,262 B2 8/2021 Tran et al.
11,160,467 B2 11/2021 Kassab et al.
11,179,169 B2 11/2021 Brouillette et al.
11,219,388 B2 1/2022 Kassab
11,246,659 B2 2/2022 Grace et al.
11,266,817 B2 3/2022 Cope et al.
11,337,713 B2 5/2022 Nguyen et al.
11,432,834 B2 9/2022 Adams
11,478,261 B2 10/2022 Nguyen
11,484,327 B2 11/2022 Anderson et al.
11,534,187 B2 12/2022 Bonutti
11,559,318 B2 1/2023 Lipowski et al.
11,559,319 B2 1/2023 Mantell
11,583,339 B2 2/2023 Schultheis
11,596,424 B2 3/2023 Hakala et al.
11,602,363 B2 3/2023 Nguyen
11,617,618 B2 4/2023 Koblish et al.
11,622,780 B2 4/2023 Nguyen et al.
11,666,348 B2 6/2023 Cioanta et al.
11,672,554 B1 6/2023 Mantell
11,696,799 B2 7/2023 Adams et al.
11,771,449 B2 10/2023 Adams et al.
11,779,363 B2 10/2023 Vo
11,839,391 B2 12/2023 Schultheis et al.
11,857,212 B2 1/2024 Capelli et al.
11,911,056 B2 2/2024 Anderson et al.
11,925,366 B2 3/2024 Cioanta et al.
11,944,331 B2 4/2024 Anderson et al.
11,950,793 B2 4/2024 Nguyen
11,996,649 B1 5/2024 Carpenter
12,004,759 B2 6/2024 Cioanta
12,004,760 B2 6/2024 Cioanta
12,005,210 B2 6/2024 Chisena et al.
12,016,610 B2 6/2024 Flores et al.
12,016,817 B2 6/2024 Engles et al.
12,035,932 B1 7/2024 Nunes et al.
12,048,445 B2 7/2024 Mantell
12,114,923 B2 10/2024 Adams et al.
12,156,668 B2 12/2024 Anderson et al.
12,178,458 B1 12/2024 Betelia et al.
12,214,147 B2 2/2025 Gianotti et al.
12,220,141 B2 2/2025 Ullmann
12,232,754 B2 2/2025 Nguyen
12,232,755 B2 2/2025 Phan et al.
12,239,332 B2 3/2025 Cioanta et al.
12,318,100 B2 6/2025 Cioanta
12,364,493 B2 7/2025 Cioanta et al.
12,364,494 B2 7/2025 Cioanta et al.
12,426,904 B2 9/2025 Nguyen et al.
12,433,619 B2 10/2025 Liu et al.
12,514,602 B2 1/2026 Schoenle
2001/0037106 A1 11/2001 Shadduck
2001/0044596 A1 11/2001 Jaafar
2002/0045890 A1 4/2002 Celliers et al.
2002/0072705 A1 6/2002 Vrba et al.
2002/0082553 A1 6/2002 Duchamp
2002/0103455 A1 8/2002 Zhang et al.
2002/0169458 A1 11/2002 Connors
2002/0177889 A1 11/2002 Brisken et al.
2002/0198521 A1 12/2002 Maguire
2003/0004434 A1 1/2003 Greco et al.
2003/0014047 A1 1/2003 Woloszko et al.
2003/0065371 A1 4/2003 Satake
2003/0135223 A1 7/2003 Teague et al.
2003/0144654 A1 7/2003 Hilal
2003/0176873 A1 9/2003 Chernenko et al.
2003/0191492 A1 10/2003 Gellman et al.
2003/0229370 A1 12/2003 Miller
2004/0006288 A1 1/2004 Spector et al.
2004/0006307 A1 1/2004 Qureshi et al.
2004/0006333 A1 1/2004 Arnold et al.
2004/0010249 A1 1/2004 Truckai et al.
2004/0024347 A1 2/2004 Wilson et al.
2004/0044308 A1 3/2004 Naimark et al.
2004/0054367 A1 3/2004 Jimenez et al.
2004/0073251 A1 4/2004 Weber
2004/0097963 A1 5/2004 Seddon
2004/0097996 A1 5/2004 Rabiner et al.
2004/0153109 A1 8/2004 Tiedtke et al.
2004/0162508 A1 8/2004 Uebelacker
2004/0167466 A1 8/2004 Drasler et al.
2004/0172110 A1 9/2004 Satake
2004/0193046 A1 9/2004 Nash et al.
2004/0215139 A1 10/2004 Cohen
2004/0249401 A1 12/2004 Rabiner et al.
2004/0254570 A1 12/2004 Hadjicostis et al.
2005/0010140 A1 1/2005 Forssmann
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0096669 A1 5/2005 Rabiner et al.
2005/0113722 A1 5/2005 Schultheiss
2005/0113822 A1 5/2005 Fuimaono et al.
2005/0159645 A1 7/2005 Bertolero et al.
2005/0171527 A1 8/2005 Bhola
2005/0194583 A1 9/2005 Taylor et al.
2005/0197667 A1 9/2005 Chan et al.
2005/0228343 A1 10/2005 Kelley
2005/0228372 A1 10/2005 Truckai et al.
2005/0228428 A1 10/2005 Ali et al.
2005/0245866 A1 11/2005 Azizi
2005/0249667 A1 11/2005 Tuszynski et al.
2005/0251131 A1 11/2005 Lesh
2005/0256410 A1 11/2005 Rabiner et al.
2005/0267467 A1 12/2005 Paul et al.
2005/0267488 A1 12/2005 Hare et al.
2005/0273130 A1 12/2005 Sell
2006/0004286 A1 1/2006 Chang et al.
2006/0041304 A1 2/2006 Jang et al.
2006/0064081 A1 3/2006 Rosinko
2006/0064082 A1 3/2006 Bonutti
2006/0069424 A1 3/2006 Acosta et al.
2006/0074484 A1 4/2006 Huber
2006/0178685 A1 8/2006 Melsheimer
2006/0184076 A1 8/2006 Gill et al.

(56) References Cited

U.S. PATENT DOCUMENTS

2006/0190022 A1 8/2006 Beyar et al.
2006/0200191 A1 9/2006 Zadno-Azizi
2006/0221528 A1 10/2006 Li et al.
2006/0235269 A1 10/2006 Waxman
2006/0241524 A1 10/2006 Lee et al.
2006/0282153 A1 12/2006 Jang
2007/0005053 A1 1/2007 Dando
2007/0016112 A1 1/2007 Schultheiss et al.
2007/0032723 A1 2/2007 Glossop
2007/0038227 A1 2/2007 Massicotte et al.
2007/0078500 A1 4/2007 Ryan et al.
2007/0088380 A1 4/2007 Hirszowicz et al.
2007/0106320 A1 5/2007 Blix et al.
2007/0123851 A1 5/2007 Alejandro et al.
2007/0129667 A1 6/2007 Tiedtke et al.
2007/0156129 A1 7/2007 Kovalcheck
2007/0198047 A1 8/2007 Schon et al.
2007/0201031 A1 8/2007 Axelrod et al.
2007/0225677 A1 9/2007 Rowe et al.
2007/0232964 A1 10/2007 Voss
2007/0239082 A1 10/2007 Schultheiss et al.
2007/0239182 A1 10/2007 Glines et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0270897 A1 11/2007 Skerven et al.
2007/0282301 A1 12/2007 Segalescu et al.
2007/0299392 A1 12/2007 Beyar et al.
2007/0299481 A1 12/2007 Syed et al.
2008/0027464 A1 1/2008 Moll et al.
2008/0039790 A1 2/2008 Hasebe
2008/0058836 A1 3/2008 Moll et al.
2008/0065013 A1 3/2008 Goodin
2008/0065014 A1 3/2008 Von et al.
2008/0097251 A1 4/2008 Babaev
2008/0183111 A1 7/2008 Voss
2008/0188803 A1 8/2008 Jang
2008/0188866 A1 8/2008 Karpiel et al.
2008/0188913 A1 8/2008 Stone et al.
2008/0200896 A1 8/2008 Shmulewitz et al.
2008/0249518 A1 10/2008 Warnking et al.
2008/0249595 A1 10/2008 McDaniel
2008/0300610 A1 12/2008 Chambers
2009/0036829 A1 2/2009 Pagel et al.
2009/0036831 A1 2/2009 Howat
2009/0041833 A1 2/2009 Bettinger et al.
2009/0054875 A1 2/2009 Strauss et al.
2009/0069748 A1 3/2009 Schaeffer
2009/0143651 A1 6/2009 Kallback et al.
2009/0157066 A1 6/2009 Satake
2009/0227992 A1 9/2009 Nir et al.
2009/0234282 A1 9/2009 Mcandrew et al.
2009/0247945 A1 10/2009 Levit et al.
2009/0254114 A1 10/2009 Hirszowicz et al.
2009/0299447 A1 12/2009 Jensen et al.
2009/0312768 A1 12/2009 Hawkins et al.
2010/0016862 A1 1/2010 Hawkins et al.
2010/0036294 A1 2/2010 Mantell et al.
2010/0082059 A1 4/2010 Gellman et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0179424 A1 7/2010 Warnking et al.
2010/0228192 A1 9/2010 O'Dea et al.
2010/0229792 A1 9/2010 Yamasaki et al.
2010/0274271 A1 10/2010 Kelley
2010/0286709 A1 11/2010 Diamant et al.
2010/0305565 A1 12/2010 Truckai et al.
2011/0028868 A1 2/2011 Spector
2011/0033807 A1 2/2011 Wang et al.
2011/0034832 A1 2/2011 Cioanta et al.
2011/0064953 A1 3/2011 O'Rourke et al.
2011/0092957 A1 4/2011 Intoccia
2011/0118634 A1 5/2011 Golan
2011/0166570 A1 7/2011 Hawkins et al.
2011/0196412 A1 8/2011 Levit et al.
2011/0208185 A1 8/2011 Diamant et al.
2011/0257523 A1 10/2011 Hastings et al.
2011/0264039 A1 10/2011 Thielen et al.
2011/0270273 A1 11/2011 Moll et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall
2012/0157991 A1 6/2012 Christian
2012/0172696 A1 7/2012 Kaellbaeck et al.
2012/0203255 A1 8/2012 Hawkins et al.
2012/0221013 A1 8/2012 Hawkins et al.
2012/0253358 A1 10/2012 Golan
2013/0030431 A1 1/2013 Adams
2013/0030447 A1 1/2013 Adams
2013/0033968 A1 2/2013 Schaefer et al.
2013/0041355 A1 2/2013 Heeren et al.
2013/0096571 A1 4/2013 Massicotte et al.
2013/0116714 A1 5/2013 Adams et al.
2013/0123694 A1 5/2013 Subramaniyan et al.
2013/0150874 A1 6/2013 Kassab
2013/0253622 A1 9/2013 Hooven
2013/0345600 A1 12/2013 Katragadda et al.
2014/0005576 A1 1/2014 Adams et al.
2014/0039513 A1 2/2014 Hakala et al.
2014/0039514 A1 2/2014 Adams et al.
2014/0046229 A1 2/2014 Hawkins et al.
2014/0046353 A1 2/2014 Adams
2014/0052145 A1 2/2014 Adams et al.
2014/0052146 A1 2/2014 Curtis et al.
2014/0052147 A1 2/2014 Hakala et al.
2014/0074076 A1 3/2014 Gertner
2014/0074111 A1 3/2014 Hakala et al.
2014/0074113 A1 3/2014 Hakala et al.
2014/0163592 A1 6/2014 Hawkins et al.
2014/0180278 A1 6/2014 Abboud et al.
2014/0214061 A1 7/2014 Adams et al.
2014/0243820 A1 8/2014 Adams et al.
2014/0243846 A1 8/2014 Aggerholm et al.
2014/0243847 A1 8/2014 Hakala et al.
2014/0257323 A1 9/2014 Mantell
2014/0288570 A1 9/2014 Adams
2015/0039002 A1 2/2015 Hawkins
2015/0073430 A1 3/2015 Hakala et al.
2015/0080995 A1 3/2015 Seeley et al.
2015/0094703 A1 4/2015 Zikorus et al.
2015/0238208 A1 8/2015 Adams et al.
2015/0238209 A1 8/2015 Hawkins et al.
2015/0320432 A1 11/2015 Adams
2016/0022295 A1 1/2016 Mantell
2016/0095610 A1 4/2016 Lipowski et al.
2016/0101280 A1 4/2016 Thakkar et al.
2016/0113674 A1 4/2016 Kelley
2016/0135828 A1 5/2016 Hawkins et al.
2016/0141892 A1 5/2016 Li et al.
2016/0151081 A1 6/2016 Adams et al.
2016/0183957 A1 6/2016 Hakala et al.
2016/0184023 A1 6/2016 Grace et al.
2016/0324534 A1 11/2016 Hawkins et al.
2016/0331389 A1 11/2016 Hakala et al.
2016/0354144 A1 12/2016 Caplan et al.
2017/0000959 A1 1/2017 Mantell et al.
2017/0020598 A1 1/2017 Millis et al.
2017/0056035 A1 3/2017 Adams
2017/0086867 A1 3/2017 Adams
2017/0135709 A1 5/2017 Nguyen et al.
2017/0258523 A1 9/2017 Adams et al.
2017/0274160 A1 9/2017 Mantell et al.
2017/0303946 A1 10/2017 Ku et al.
2017/0311965 A1 11/2017 Adams
2018/0028208 A1 2/2018 Adams et al.
2018/0098779 A1 4/2018 Betelia et al.
2018/0153568 A1 6/2018 Kat-Kuoy
2018/0214166 A1 8/2018 Mantell
2018/0256250 A1 9/2018 Adams et al.

(56) References Cited

U.S. PATENT DOCUMENTS

2018/0303501 A1 10/2018 Hawkins
2018/0304053 A1 10/2018 Eggert et al.
2018/0317946 A1 11/2018 Adams et al.
2018/0360482 A1 12/2018 Nguyen
2019/0000491 A1 1/2019 Schoenle
2019/0069916 A1 3/2019 Hawkins et al.
2019/0150960 A1 5/2019 Nguyen et al.
2019/0175198 A1 6/2019 Ku et al.
2019/0254607 A1 8/2019 Kllbck et al.
2019/0254692 A1 8/2019 Hakala et al.
2019/0262594 A1 8/2019 Ogata et al.
2019/0269426 A1 9/2019 Hakala et al.
2019/0365400 A1 12/2019 Adams et al.
2019/0388110 A1 12/2019 Nguyen et al.
2020/0000484 A1 1/2020 Hawkins
2020/0022716 A1 1/2020 Hakala et al.
2020/0038044 A1 2/2020 Lipowski et al.
2020/0085458 A1 3/2020 Nguyen et al.
2020/0085459 A1 3/2020 Adams
2020/0100803 A1 4/2020 Mantell
2020/0129195 A1 4/2020 Mcgowan et al.
2020/0129741 A1 4/2020 Kawwas et al.
2020/0129742 A1 4/2020 Cope et al.
2020/0246032 A1 8/2020 Betelia et al.
2020/0281505 A1 9/2020 Kassab et al.
2020/0289767 A1 9/2020 Mantell et al.
2020/0297280 A1 9/2020 Kllbck et al.
2020/0297366 A1 9/2020 Nguyen et al.
2020/0383724 A1 12/2020 Adams et al.
2020/0397453 A1 12/2020 Mcgowan et al.
2020/0398033 A1 12/2020 Mcgowan et al.
2020/0406010 A1 12/2020 Massimini et al.
2021/0038237 A1 2/2021 Adams
2021/0059751 A1 3/2021 Zhang et al.
2021/0085347 A1 3/2021 Phan et al.
2021/0085348 A1 3/2021 Nguyen
2021/0085349 A1 3/2021 Cioanta et al.
2021/0085350 A1 3/2021 Cioanta et al.
2021/0085383 A1 3/2021 Vo et al.
2021/0093342 A1 4/2021 Cioanta et al.
2021/0128241 A1 5/2021 Schultheis
2021/0177445 A1 6/2021 Nguyen
2021/0186613 A1 6/2021 Cook et al.
2021/0220052 A1 7/2021 Cook
2021/0228137 A1 7/2021 Aujla
2021/0267615 A1 9/2021 Cioanta et al.
2021/0267685 A1 9/2021 Schultheis et al.
2021/0275247 A1 9/2021 Schultheis et al.
2021/0282792 A1 9/2021 Adams et al.
2021/0290259 A1 9/2021 Hakala et al.
2021/0290305 A1 9/2021 Cook et al.
2021/0308001 A1 10/2021 Cioanta
2021/0310786 A1 10/2021 Zhang et al.
2021/0330384 A1 10/2021 Cook et al.
2021/0338258 A1 11/2021 Hawkins et al.
2021/0378743 A1 12/2021 Massimini et al.
2022/0008129 A1 1/2022 Hancock et al.
2022/0015785 A1 1/2022 Hakala et al.
2022/0054194 A1 2/2022 Bacher et al.
2022/0071692 A1 3/2022 Govari et al.
2022/0104875 A1 4/2022 Gleiman et al.
2022/0125453 A1 4/2022 Nguyen
2022/0152321 A1 5/2022 Haber et al.
2022/0152364 A1 5/2022 Cope et al.
2022/0183708 A1 6/2022 Phan et al.
2022/0240958 A1 8/2022 Nguyen et al.
2022/0273324 A1 9/2022 Schultheis
2022/0273916 A1 9/2022 Kawwas et al.
2022/0280765 A1 9/2022 Tabiliran et al.
2022/0287731 A1 9/2022 Tan et al.
2022/0287732 A1 9/2022 Anderson et al.
2022/0291442 A1 9/2022 De et al.
2022/0313359 A1 10/2022 Schultheis et al.
2022/0331012 A1 10/2022 Bumpus
2022/0338890 A1 10/2022 Anderson et al.
2022/0339428 A1 10/2022 Porterfield et al.
2022/0354578 A1 11/2022 Cook et al.
2023/0028890 A1 1/2023 Cioanta
2023/0040190 A1 2/2023 Batchelder et al.
2023/0043475 A1 2/2023 Adams
2023/0044926 A1 2/2023 Batchelder et al.
2023/0064371 A1 3/2023 Cook et al.
2023/0107690 A1 4/2023 Nguyen
2023/0110647 A1 4/2023 Buscaglia et al.
2023/0111554 A1 4/2023 Lulian
2023/0165598 A1 6/2023 Nguyen et al.
2023/0293195 A1 9/2023 Lipowski et al.
2023/0293196 A1 9/2023 Robert
2023/0293197 A1 9/2023 Nguyen et al.
2023/0310054 A1 10/2023 Schultheis
2023/0310073 A1 10/2023 Adams et al.
2023/0329731 A1 10/2023 Hakala et al.
2023/0363774 A1 11/2023 Cioanta et al.
2023/0380849 A1 11/2023 Adams et al.
2023/0404605 A1 12/2023 Vo
2023/0414234 A1 12/2023 Anderson et al.
2024/0016508 A1 1/2024 Kocur
2024/0099734 A1 3/2024 Capelli et al.
2024/0156476 A1 5/2024 Staab et al.
2024/0156478 A1 5/2024 Ballard et al.
2024/0188973 A1 6/2024 Cioanta et al.
2024/0188975 A1 6/2024 Nguyen
2024/0189030 A1 6/2024 Cook et al.
2024/0189543 A1 6/2024 Salinas et al.
2024/0206896 A1 6/2024 Ingersoll et al.
2024/0206972 A1 6/2024 Sun et al.
2024/0216062 A1 7/2024 Cook et al.
2024/0252191 A1 8/2024 Cioanta et al.
2024/0252192 A1 8/2024 Anderson et al.
2024/0268842 A1 8/2024 Phan et al.
2024/0277374 A1 8/2024 Varilla et al.
2024/0277410 A1 8/2024 Cook
2024/0285295 A1 8/2024 Cioanta
2024/0285296 A1 8/2024 Vo
2024/0293282 A1 9/2024 Engles et al.
2024/0299051 A1 9/2024 Sidhu et al.
2024/0335206 A1 10/2024 Liu et al.
2024/0350154 A1 10/2024 Nunes et al.
2024/0366245 A1 11/2024 Schoenle
2024/0423654 A1 12/2024 Ji et al.
2025/0000532 A1 1/2025 Jens
2025/0064471 A1 2/2025 Hasenberg et al.
2025/0072967 A1 3/2025 Hasenberg et al.
2025/0160862 A1 5/2025 Betelia et al.
2025/0169835 A1 5/2025 Kerlo et al.
2025/0176984 A1 6/2025 Hasenberg et al.
2025/0228578 A1 7/2025 Hakala et al.
2025/0228579 A1 7/2025 Nguyen et al.
2025/0268617 A1 8/2025 Rond et al.
2025/0275782 A1 9/2025 Hasenberg et al.
2025/0303109 A1 10/2025 Johnson et al.

FOREIGN PATENT DOCUMENTS

AU 2007254353 A1 11/2007
AU 2009257368 A1 12/2009
AU 2009313507 B2 11/2014
AU 2013284490 A1 1/2015
AU 2013315444 B2 8/2017
AU 2018204691 B2 6/2019
CA 2104414 A1 2/1995
CA 2613360 A1 1/2007
CA 2652381 A1 11/2007
CA 2727429 A1 12/2009
CA 2779600 A1 5/2010
CN 1204242 A 1/1999
CN 1269708 A 10/2000
CN 1161081 C 8/2004
CN 1942145 A 4/2007
CN 101043914 A 9/2007
CN 101495023 A 7/2009
CN 201629723 U 11/2010
CN 102057422 A 5/2011
CN 102271748 A 12/2011

(56) References Cited

FOREIGN PATENT DOCUMENTS

| | | | |
|---|---|---|---|
| CN | 102355856 | A | 2/2012 |
| CN | 102765785 | A | 11/2012 |
| CN | 203564304 | U | 4/2014 |
| CN | 107633840 | A | 1/2018 |
| CN | 208694015 | U | 4/2019 |
| CN | 109965922 | A | 7/2019 |
| CN | 209548049 | U | 10/2019 |
| CN | 209996422 | U | 1/2020 |
| CN | 110811761 | A | 2/2020 |
| CN | 111067591 | A | 4/2020 |
| CN | 111184553 | A | 5/2020 |
| CN | 211094481 | U | 7/2020 |
| CN | 211094508 | U | 7/2020 |
| CN | 111388086 | B | 8/2020 |
| CN | 111568500 | A | 8/2020 |
| CN | 111568539 | A | 8/2020 |
| CN | 111969882 | A | 11/2020 |
| CN | 212491104 | U | 2/2021 |
| CN | 112516439 | A | 3/2021 |
| CN | 112618922 | A | 4/2021 |
| CN | 112674838 | A | 4/2021 |
| CN | 112754645 | A | 5/2021 |
| CN | 112842460 | A | 5/2021 |
| CN | 112869825 | A | 6/2021 |
| CN | 112869826 | A | 6/2021 |
| CN | 112869827 | A | 6/2021 |
| CN | 112932609 | A | 6/2021 |
| CN | 113117220 | A | 7/2021 |
| CN | 113244506 | A | 8/2021 |
| CN | 113288335 | A | 8/2021 |
| CN | 113289212 | A | 8/2021 |
| CN | 113289216 | A | 8/2021 |
| CN | 306761244 | S | 8/2021 |
| CN | 113332568 | A | 9/2021 |
| CN | 113332569 | A | 9/2021 |
| CN | 113332570 | A | 9/2021 |
| CN | 113349882 | A | 9/2021 |
| CN | 113349982 | A | 9/2021 |
| CN | 113398444 | A | 9/2021 |
| CN | 113440215 | A | 9/2021 |
| CN | 113558715 | A | 10/2021 |
| CN | 113598878 | A | 11/2021 |
| CN | 113633347 | A | 11/2021 |
| CN | 113730768 | A | 12/2021 |
| CN | 113842190 | A | 12/2021 |
| CN | 113855153 | A | 12/2021 |
| CN | 215067917 | U | 12/2021 |
| CN | 215228131 | U | 12/2021 |
| CN | 215384399 | U | 1/2022 |
| CN | 215384400 | U | 1/2022 |
| CN | 215386905 | U | 1/2022 |
| CN | 215458400 | U | 1/2022 |
| CN | 215458401 | U | 1/2022 |
| CN | 215505065 | U | 1/2022 |
| CN | 215537694 | U | 1/2022 |
| CN | 215584286 | U | 1/2022 |
| CN | 215606068 | U | 1/2022 |
| CN | 215651394 | U | 1/2022 |
| CN | 215653328 | U | 1/2022 |
| CN | 215688241 | U | 2/2022 |
| CN | 215739273 | U | 2/2022 |
| CN | 215900676 | U | 2/2022 |
| CN | 114098896 | A | 3/2022 |
| CN | 114098897 | A | 3/2022 |
| CN | 114098898 | A | 3/2022 |
| CN | 114209960 | A | 3/2022 |
| CN | 215960130 | U | 3/2022 |
| CN | 216061635 | U | 3/2022 |
| CN | 216495498 | U | 5/2022 |
| CN | 307361122 | S | 5/2022 |
| CN | 217040236 | U | 7/2022 |
| CN | 217066519 | U | 7/2022 |
| CN | 307436397 | S | 7/2022 |
| CN | 112971914 | B | 8/2022 |
| CN | 114831697 | A | 8/2022 |
| CN | 217138101 | U | 8/2022 |
| CN | 217162846 | U | 8/2022 |
| CN | 115051691 | A | 9/2022 |
| CN | 115137444 | A | 10/2022 |
| CN | 115149929 | A | 10/2022 |
| CN | 115153753 | A | 10/2022 |
| CN | 115154852 | A | 10/2022 |
| CN | 115192872 | A | 10/2022 |
| CN | 217611283 | U | 10/2022 |
| CN | 115252050 | A | 11/2022 |
| CN | 115389852 | A | 11/2022 |
| CN | 115463317 | A | 12/2022 |
| CN | 218391846 | U | 1/2023 |
| CN | 115737062 | A | 3/2023 |
| CN | 218899599 | U | 4/2023 |
| CN | 115944355 | B | 6/2023 |
| CN | 116392203 | B | 9/2023 |
| CN | 117462207 | A | 1/2024 |
| DE | 2635635 | A1 | 2/1978 |
| DE | 3038445 | A1 | 5/1982 |
| DE | 3536073 | A1 | 4/1987 |
| DE | 3900433 | A1 | 7/1990 |
| DE | 3930600 | A1 | 4/1991 |
| DE | 4005743 | A1 | 8/1991 |
| DE | 4007295 | A1 | 9/1991 |
| DE | 4012642 | A1 | 10/1991 |
| DE | 4120259 | A1 | 12/1992 |
| DE | 29724174 | U1 | 4/2000 |
| DE | 10010467 | A1 | 9/2001 |
| DE | 102004053549 | A1 | 5/2006 |
| DE | 202006014285 | U1 | 12/2006 |
| DE | 102006002412 | A1 | 7/2007 |
| EP | 0249338 | A2 | 12/1987 |
| EP | 0311295 | A2 | 4/1989 |
| EP | 0313836 | A2 | 5/1989 |
| EP | 0351240 | A2 | 1/1990 |
| EP | 0382392 | A1 | 8/1990 |
| EP | 0442199 | A2 | 8/1991 |
| EP | 0547146 | A1 | 6/1993 |
| EP | 0558297 | A2 | 9/1993 |
| EP | 0571306 | A1 | 11/1993 |
| EP | 0647435 | A1 | 4/1995 |
| EP | 0704226 | A1 | 4/1996 |
| EP | 0623360 | B1 | 3/1999 |
| EP | 1898775 | A2 | 3/2008 |
| EP | 2023796 | A2 | 2/2009 |
| EP | 2043501 | A2 | 4/2009 |
| EP | 2046227 | A2 | 4/2009 |
| EP | 1009303 | B1 | 6/2009 |
| EP | 2120736 | A1 | 11/2009 |
| EP | 2253884 | A1 | 11/2010 |
| EP | 2300091 | A2 | 3/2011 |
| EP | 2362798 | A2 | 9/2011 |
| EP | 2032201 | B1 | 4/2013 |
| EP | 2866689 | A1 | 5/2015 |
| EP | 2879607 | A1 | 6/2015 |
| EP | 2884911 | B1 | 6/2016 |
| EP | 3487414 | A2 | 5/2019 |
| EP | 3641672 | A1 | 4/2020 |
| EP | 2895086 | B1 | 5/2021 |
| EP | 4110213 | A1 | 1/2023 |
| EP | 4199849 | A1 | 6/2023 |
| EP | 3960099 | B1 | 8/2023 |
| EP | 4387540 | A1 | 6/2024 |
| EP | 4391946 | A1 | 7/2024 |
| EP | 4406496 | A1 | 7/2024 |
| EP | 4423863 | A1 | 9/2024 |
| EP | 4431032 | A1 | 9/2024 |
| FR | 2412301 | A1 | 7/1979 |
| FR | 2593382 | A1 | 7/1987 |
| FR | 2738381 | A1 | 3/1997 |
| JP | 58-032755 | A | 2/1983 |
| JP | 60-191353 | U | 12/1985 |
| JP | 61-146251 | A | 7/1986 |
| JP | 62-009921 | U | 1/1987 |
| JP | 62-060547 | A | 3/1987 |
| JP | 62-099210 | U | 6/1987 |
| JP | 62-275446 | A | 11/1987 |
| JP | 03-063059 | A | 3/1991 |

(56) References Cited

FOREIGN PATENT DOCUMENTS

| | | | |
|---|---|---|---|
| JP | 06-070984 | A | 3/1994 |
| JP | 06-125915 | A | 5/1994 |
| JP | 07-047135 | A | 2/1995 |
| JP | 08-089511 | A | 4/1996 |
| JP | 10-099444 | A | 4/1998 |
| JP | 10-314177 | A | 12/1998 |
| JP | 10-513379 | A | 12/1998 |
| JP | 2002-538932 | A | 11/2002 |
| JP | 2003-102850 | A | 4/2003 |
| JP | 2004-081374 | A | 3/2004 |
| JP | 2004-223080 | A | 8/2004 |
| JP | 2004-357792 | A | 12/2004 |
| JP | 2005-501597 | A | 1/2005 |
| JP | 2005-095410 | A | 4/2005 |
| JP | 2005-515825 | A | 6/2005 |
| JP | 2006-516465 | A | 7/2006 |
| JP | 2007-054480 | A | 3/2007 |
| JP | 2007-289707 | A | 11/2007 |
| JP | 2007-532182 | A | 11/2007 |
| JP | 2008-506447 | A | 3/2008 |
| JP | 4072580 | B2 | 4/2008 |
| JP | 2009-537222 | A | 10/2009 |
| JP | 4491149 | B2 | 6/2010 |
| JP | 2011-513694 | A | 4/2011 |
| JP | 2011-520248 | A | 7/2011 |
| JP | 2011-524203 | A | 9/2011 |
| JP | 2011-528963 | A | 12/2011 |
| JP | 2012-505050 | A | 3/2012 |
| JP | 2012-508042 | A | 4/2012 |
| JP | 2014-208305 | A | 11/2014 |
| JP | 5636363 | B2 | 12/2014 |
| JP | 2015-525657 | A | 9/2015 |
| JP | 2015-528327 | A | 9/2015 |
| JP | 6029828 | B2 | 11/2016 |
| JP | 6081510 | B2 | 2/2017 |
| JP | 6104375 | B2 | 3/2017 |
| JP | 6257625 | B2 | 1/2018 |
| JP | 6278530 | B2 | 2/2018 |
| JP | 6364011 | B2 | 7/2018 |
| JP | 6529565 | B2 | 6/2019 |
| JP | 7142035 | B2 | 9/2022 |
| JP | 7277060 | B2 | 5/2023 |
| JP | 7364735 | B2 | 10/2023 |
| WO | 89/11307 | A1 | 11/1989 |
| WO | 91/10228 | A1 | 7/1991 |
| WO | 91/10403 | A1 | 7/1991 |
| WO | 92/03975 | A1 | 3/1992 |
| WO | 95/10232 | A1 | 4/1995 |
| WO | 96/24297 | A1 | 8/1996 |
| WO | 97/21460 | A1 | 6/1997 |
| WO | 98/33171 | A2 | 7/1998 |
| WO | 99/00060 | A1 | 1/1999 |
| WO | 99/02096 | A1 | 1/1999 |
| WO | 99/21611 | A1 | 5/1999 |
| WO | 00/33913 | A2 | 6/2000 |
| WO | 00/50115 | A2 | 8/2000 |
| WO | 00/51511 | A1 | 9/2000 |
| WO | 00/56237 | A2 | 9/2000 |
| WO | 01/24712 | A1 | 4/2001 |
| WO | 03/51450 | A1 | 6/2003 |
| WO | 03/86236 | A2 | 10/2003 |
| WO | 03/86525 | A1 | 10/2003 |
| WO | 2004/069072 | A2 | 8/2004 |
| WO | 2005/053532 | A1 | 6/2005 |
| WO | 2005/099594 | A1 | 10/2005 |
| WO | 2005/102199 | A1 | 11/2005 |
| WO | 2006/006169 | A2 | 1/2006 |
| WO | 2006/060492 | A2 | 6/2006 |
| WO | 2006/127158 | A2 | 11/2006 |
| WO | 2007/002079 | A2 | 1/2007 |
| WO | 2007/022055 | A1 | 2/2007 |
| WO | 2007/052341 | A1 | 5/2007 |
| WO | 2007/053967 | A1 | 5/2007 |
| WO | 2007/086965 | A2 | 8/2007 |
| WO | 2007/088546 | A2 | 8/2007 |
| WO | 2007/136599 | A2 | 11/2007 |
| WO | 2007/149905 | A2 | 12/2007 |
| WO | 2008/014425 | A2 | 1/2008 |
| WO | 2008/017080 | A2 | 2/2008 |
| WO | 2008/097833 | A1 | 8/2008 |
| WO | 2009/121017 | A1 | 10/2009 |
| WO | 2009/126544 | A1 | 10/2009 |
| WO | 2009/128061 | A2 | 10/2009 |
| WO | 2009/136268 | A2 | 11/2009 |
| WO | 2009/152352 | A2 | 12/2009 |
| WO | 2010/014515 | A2 | 2/2010 |
| WO | 2010/054048 | A2 | 5/2010 |
| WO | 2011/006017 | A1 | 1/2011 |
| WO | 2011/094111 | A2 | 8/2011 |
| WO | 2011/143468 | A3 | 3/2012 |
| WO | 2012/025833 | A2 | 3/2012 |
| WO | 2012/064404 | A1 | 5/2012 |
| WO | 2012/106259 | A2 | 8/2012 |
| WO | 2013/059735 | A1 | 4/2013 |
| WO | 2013/070750 | A1 | 5/2013 |
| WO | 2013/169807 | A1 | 11/2013 |
| WO | 2014/004887 | A1 | 1/2014 |
| WO | 2014/025397 | A1 | 2/2014 |
| WO | 2014/025620 | A1 | 2/2014 |
| WO | 2014/025981 | A1 | 2/2014 |
| WO | 2014/028885 | A1 | 2/2014 |
| WO | 2014/043400 | A1 | 3/2014 |
| WO | 2015/017499 | A1 | 2/2015 |
| WO | 2015/167360 | A1 | 11/2015 |
| WO | 2016/130713 | A1 | 8/2016 |
| WO | 2018/200865 | A1 | 11/2018 |
| WO | 2019/099218 | A1 | 5/2019 |
| WO | 2019/174625 | A1 | 9/2019 |
| WO | 2020/048274 | A1 | 3/2020 |
| WO | 2020/192146 | A1 | 10/2020 |
| WO | 2021/022849 | A1 | 2/2021 |
| WO | 2021/025624 | A1 | 2/2021 |
| WO | 2021/061294 | A1 | 4/2021 |
| WO | 2021/061451 | A1 | 4/2021 |
| WO | 2021/061523 | A1 | 4/2021 |
| WO | 2021/122491 | A1 | 6/2021 |
| WO | 2022/055784 | A1 | 3/2022 |
| WO | 2022/127506 | A1 | 6/2022 |
| WO | 2022/127507 | A1 | 6/2022 |
| WO | 2022/127509 | A1 | 6/2022 |
| WO | 2022/166883 | A1 | 8/2022 |
| WO | 2022/186783 | A1 | 9/2022 |
| WO | 2022/217917 | A1 | 10/2022 |
| WO | 2023/015047 | A1 | 2/2023 |
| WO | 2023/015295 | A1 | 2/2023 |
| WO | 2023/029191 | A1 | 3/2023 |
| WO | 2023/083084 | A1 | 5/2023 |
| WO | 2024/049814 | A1 | 3/2024 |
| WO | 2024/081361 | A1 | 4/2024 |
| WO | 2024/102896 | A2 | 5/2024 |
| WO | 2024/107418 | A1 | 5/2024 |
| WO | 2024/107470 | A1 | 5/2024 |
| WO | 2024/138037 | A2 | 6/2024 |
| WO | 2024/138212 | A1 | 6/2024 |
| WO | 2024/206827 | A2 | 10/2024 |
| WO | 2024/216050 | A2 | 10/2024 |
| WO | 2025/054289 | A1 | 3/2025 |

OTHER PUBLICATIONS

BAIM., "Grossman's Cardiac Catheterization, Angiography, and Intervention," Seventh Edition, 2005, 6 pages.

BAIM., "Percutaneous Balloon Angioplasty and General Coronary Intervention," Chapter 22, 2005, pp. 433-466.

Basavarajaiah, S et al., "To evaluate the impact of dose dependency on calcium fractures from the shockwave balloon in calcified lesions" [PowerPoint Presentation], Transcatheter Cardiovascular Therapeutics Conference, San Francisco, CA, United States, Oct. 25-28, 2025.

Begun, Frank P., "Modes of Intracorporeal Lithotripsy: Ultrasound Versus Electrohydraulic Lithotripsy Versus Laser Lithotripsy", Seminars in Urology, vol. 12, No. 1, Feb. 1994, pp. 39-50.

(56) References Cited

OTHER PUBLICATIONS

Bertrand et al., "Percutaneous Transluminal Coronary Rotary Ablation with Rotablator (European Experience)", The American Journal of Cardiology, vol. 69, Feb. 15, 1992, pp. 470-474.
Briggs, C., et al., "The New Shockwave L6 Peripheral Intravascular Lithotripsy (IVL) Catheter", Endovascular Today, May 2023.
Brinton, T. D., et al., "Abstract 12272: Ultrasound Mediated Renal Sympathetic Denervation", Circulation, vol. 124, No. 21, Nov. 22, 2011.
Brinton, T. J., et al., "Current use of imaging in cardiac stem cell clinical trials.", Current Cardiovascular Imaging Reports, vol. 2, No. 1, 2009, pp. 1-2.
Brinton, T. J., et al., "Outcomes from a postgraduate biomedical technology innovation training program: the first 12 years of Stanford Biodesign.", Annals of biomedical engineering, vol. 41, 2013, pp. 1803-1810.
Chan et al., "A Perspective on Laser Lithotripsy: The Fragmentation Processes", Journal of Endourology, vol. 15, No. 3, Apr. 2001, pp. 257-273.
Choi et al., "Low Power Ultrasound Delivered Through a PTCA-Like Guidewire: Preclinical Feasibility and Safety of a Novel Technology for Intracoronary Thrombolysis," Journal of Interventional Cardiology, vol. 19, Issue 1, 2006, pp. 87-92.
Cleveland, R.O .; McAteer, J.A. "Physics of Shock-Wave Lithotripsy". In Smith's Textbook of Endourology; Wiley: Hoboken, Nj, USA, 2012; pp. 317-332.
Compare Materials, from MatWeb, retrieved from https://www.matweb.com, accessed on Feb. 26, 2024, 5 pp.
Corl, J. D., et al., "First Human Use of Shockwave L6 Intravascular Lithotripsy Catheter in Severely Calcified Large Vessel Stenoses", Journal of the Society for Cardiovascular Angiography & Interventions, vol. 2, Issue 4, May 2023.
Dash R., et al., "Abstract 12435: Detection of Injured Border Zone Myocardium Using Manganese-Enhanced and Delayed-Enhanced MRI in a Pig Ischemia-Reperfusion Model", Circulation, vol. 122, Supp. 21, Nov. 23, 2010.
Dash, R., et al., "Dual manganese-enhanced and delayed gadolinium-enhanced MRI detects myocardial border zone injury in a pig ischemia-reperfusion model.", Circulation: Cardiovascular Imaging, vol. 4, No. 5, 2011, pp. 574-582.
Davies, R., "You Asked; Shockwave C2 Aero Delivered: Shockwave's Next Coronary Catheter" [PowerPoint Presentation], Transcatheter Cardiovascular Therapeutics Conference, San Francisco, CA, United States, Oct. 25-28, 2025.
Dervan et al., "Transluminal angioplasty of occluded coronary arteries: use of a movable guide wire system", Circulation 68, No. 4, 1983, pp. 776-784.
Ernst et al., "Ability of High-Intensity Ultrasound to Ablate Human Atherosclerotic Plaques and Minimize Debris Size," The American journal of cardiology, vol. 68, Issue 2, 1991, pp. 242-246.
Extended European Search Report dated Jul. 22, 2022 in European Patent Application No. 22168972.2.
Extended European Search Report dated Jul. 25, 2022 in European Patent Application No. 22167795.8.
Extended European Search Report dated Jul. 25, 2022 in European Patent Application No. 22167806.3.
Extended European Search Report dated Jul. 15, 2022 in European Patent Application No. 22167569.7.
Extended European Search Report dated Jul. 19, 2022 in European Patent Application No. 22168990.4.
Extended European Search Report dated Jul. 22, 2022 in European Patent Application No. 22169681.8.
Extended European Search Report dated Jul. 25, 2022 in European Patent Application No. 22167815.4.
Extended European Search Report dated Jul. 25, 2022 in European Patent Application No. 22168984.7.
Fuh, E., et al., "Bone marrow stem cells for the treatment of ischemic heart disease: a clinical trial review.", Journal of Cardiovascular Translational Research, vol. 2, 2009, pp. 202-218.
Gavin et al., "An acoustic fluid-structure simulation of a therapeutic ultrasound wire waveguide apparatus," 11th International Conference on Computational Biogengineering, 2005, 14 pages.
Gerdesmeyer et al., "Physical and technical basics of extracorporeal shock wave therapy (ESWT)," The orthopedist, vol. 7, Issue 31, 2002, pp. 610-617. (English abstract).
Gravenstein D., "Extracorporeal shock wave lithotripsy and percutaneous nephrolithotomy", Anesthesia and Renal Considerations, vol. 18, No. 4, Dec. 2000, pp. 953-971.
GRECH., "Percutaneous coronary intervention. I: History and development," Bmj, vol. 326, Issue 7398, 2003, pp. 1080-1082.
Grocela et al., "Intracorporeal Lithotripsy: Instrumentation and Development", Urologic Clinics of North America, vol. 24, No. 1, Feb. 1997, pp. 13-23.
Gunn et al., "New developments in percutaneous coronary intervention," BMJ, vol. 327, Issue 7407, 2003, pp. 150-153.
Harston et al., "Safety and Success of the Beginning Percutaneous Transluminal Coronary Angioplasty Program Using the Steerable Guidewire System", Coronary Angioplasty With Steerable Guidewire, vol. 57, Apr. 1, 1986, pp. 717-720.
Hong, S. J., et al., "Intracoronary and retrograde coronary venous myocardial delivery of adipose-derived stem cells in swine infarction lead to transient myocardial trapping with predominant pulmonary redistribution.", Catheterization and Cardiovascular Interventions, vol. 83, No. 1, 2014, pp. E17-E25.
International Application No. PCT/US2024/022239, filed Mar. 29, 2014.
International Application No. PCT/US2024/024296, filed Apr. 12, 2024.
International Application No. PCT/US2024/025362, filed Apr. 19, 2024.
International Application No. PCT/US2024/025369, filed Apr. 19, 2024.
International Preliminary Report on Patentability for dated Aug. 11, 2022 for PCT Application Serial No. PCT/US2022/071341, Filed Mar. 25, 2022.
International Preliminary Report on Patentability mailed Feb. 6, 2024 for PCT Application Serial No. PCT/US2022/074607, Filed Aug. 5, 2022.
International Search Report and Written Opinion issued in PCT application No. PCT/US2022/71341, dated Aug. 11, 2022.
International Search Report and Written Opinion issued in PCT/US2021/71726, dated Feb. 7, 2022.
International Search Report and Written Opinion of International Application No. PCT/US2023/85515, mailed Jun. 13, 2024, 10 pp.
International Search Report and Written Opinion of International Application No. PCT/US2024/022239, mailed Jul. 26, 2024, 8 pp.
International Search Report and Written Opinion of International Application No. PCT/US2024/024296, mailed Aug. 21, 2024, 14 pp.
International Search Report and Written Opinion of International Application No. PCT/US2024/025362, mailed Jul. 23, 2024, 12 pp.
International Search Report and Written Opinion of International Application No. PCT/US2024/025369, mailed Jul. 23, 2024, 11 pp.
Galougahi, K.K., et al., "Intravascular Lithotripsy in Cardiovascular Interventions", American College of Cardiology, Jul. 2020.
Li, G., et al., "Evaluation of an experimental electrohydraulic discharge device for extracorporeal shock wave lithotripsy: Pressure field of sparker array", The Journal of the Acoustical Society of America, vol. 142, Issue 5, Nov. 2017, pp. 3147-3153.
International Search Report and Written Opinion of International Application No.PCT/US2023/035025, mailed Jan. 18, 2024, 11 pp.
International Search Report and Written Opinion of International Application No.PCT/US2023/037234, mailed Mar. 12, 2024, 8 pp.
International Search Report and Written Opinion received for International Patent Application No. PCT/US2022/078216, mailed on Feb. 1, 2023, 6 pages.
International Search Report and Written Opinion, mailed Apr. 12, 2024 for PCT Application Serial No. PCT/US2023/079209, filed Nov. 9, 2023.
International Search Report and Written Opinion, mailed Feb. 22, 2024, for PCT Application Serial No. PCT/US23/73648, filed Sep. 7, 2023.

(56) References Cited

OTHER PUBLICATIONS

International Search Report and Written Opinion, mailed May 28, 2024, for PCT Application Serial No. PCT/US23/085868, filed Dec. 23, 2024.
International Search Report issued in PCT/US2022/74607, mailed Oct. 25, 2022.
Judgment, Final Written Decision Determining All Challenged Claims Unpatentable Denying Petitioner's Motion to Exclude Denying Patent Owner's Motion to Exclude, 35 U.S.C. Section 318(a); 37 C.F.R. Section 42.64, Paper 75, IPR2019-00409, in U.S. Pat. No. 8,728,091 B2, dated Jul. 8, 2020.
Judgment, Final Written Decision Determining All Challenged Claims Unpatentable Denying Petitioner's Motion to Exclude Denying Petitioner's Motion to Exclude Denying Patent Owner's Motion to Exclude 35 U.S.C. Section 318(a), 37 C.F.R. Section 42.64, Paper 70, IPR2019-00408, in U.S. Pat. No. 9,642,673 B2, Entered Jul. 20, 2020.
Judgment, Final Written Decision Determining Some Challenged Claims Unpatentable Denying Petitioner's Motion to Exclude 35 U.S.C. Section 318(a), 37 C.F.R. Section 42.64, Paper 75, IPR2019-00405, in U.S. Pat. No. 8,956,371 B2, dated Jul. 8, 2020.
Kaltenbach, "The long wire technique—a new technique for steerable balloon catheter dilatation of coronary artery stenoses", European Heart Journal, vol. 5, 1984, pp. 1004-1009.
Kereiakes et al., "Principles of Intravascular Lithotripsy for Calcific Plaque Modification", JACC: Cardiovascular Interventions, vol. 14, No. 12, Jun. 28, 2021, pp. 1275-1292.
Kodama et al. "Innovative technology for tissue disruption by explosive-induced shock waves", Ultrasound in Medicine & Biology vol. 24, No. 9, 1998, pp. 1459-1460.
Lee et al., "Intravascular Lithotripsy for Calcified Left Main Artery Disease", Journal of the Society for Cardiovascular Angiography and Interventions, vol. 2, 2023, pp. 1-6.
Lee et al., "Intravascular steerable guidewire for fiberoptic laser-heated metal cautery cap in dissolution of human atherosclerotic coronary disease," American Heart Journal, vol. 110, Issue 6, 1985, pp. 1304-1306.
Levin et al., "Percutaneous Transluminal Coronary Angioplasty with an Over-the-Wire System," Radiology, vol. 155, Issue 2, 1985, pp. 323-326.
Lingeman, J. E., et al., "Shock wave lithotripsy: Advances in technology and technique." Nature Reviews Urology, vol. 6, Dec. 2009, pp. 660-670.
Litvack et al., "Percutaneous excimer laser coronary angioplasty: results in the first consecutive 3,000 patients," Journal of the American College of Cardiology, vol. 23, Issue 2, 1994, pp. 323-329.
Llewellyn-Jones, F., "The Mechanism of Electrode Erosion in Electrical Discharges: Physical Basis of the Low Erosion Rate of the Platinum Metals", Platinum Metals Review, vol. 7, Issue 2, Jan. 1963, pp. 58-65.
Loske, A. M. (2007). Shock Wave Physics for Urologists. Centro de Física Aplicada y Tecnología Avanzada, National Autonomous University of Mexico. ISBN 978-970-32-4377-8.
Lumsden et al., "Endovascular Therapy Principles of Peripheral Interventions," Blackwell Futura, 2006, 310 pages.
Mariani., "Combined Electrohydraulic and Holmium: Yag Laser Ureteroscopic Nephrolithotripsy For 20 TO 40 Mm Renal Calculi," The Journal of urology, vol. 172, Issue 1, 2004, pp. 170-174.
Mcauley et al., "Advances in guidewire technology," The American Journal of Cardiology, vol. 53, Issue 12, 1984, pp. C94-C96.
Miller et al., "Electrohydraulic Nephrolithotripsy: a Preferable Alternative to Ultrasound?", British Journal of Urology, vol. 56, 1984, pp. 589-593.
MILLER., "Endoscopic application of shock wave technology for the destruction of renal calculi" World Journal of Urology, vol. 3, 1985, pp. 36-40.
Mishra, A., et al., "RevaTen platelet-rich plasma improves cardiac function after myocardial injury.", Cardiovascular Revascularization Medicine, vol. 12, No. 3, 2011, pp. 158-163.
Mohiuddin et al., "General principles of endovascular therapy" in Endovascular Therapy: Principles of Peripheral Interventions, pp. 1-19 (2006).
Müller-Leisse. et al., "Effectiveness and safety of ultrasonic atherosclerotic plaque ablation: In vitro investigation," Cardiovascular and interventional radiology, vol. 16, 1993, pp. 303-307.
Neuzil, P., et al., "TCT-61 Optimized external focused ultrasound for renal sympathetic denervation-Wave II trial.", Journal of the American College of Cardiology, vol. 62, No. 18S1, 2013.
Nimgaonkar, A., et al., "Gastroenterology and biodesign: contributing to the future of our specialty.", Gastroenterology, vol. 144, No. 2, 2013, pp. 258-262.
Northgate Technologies, Northgate Autolith pulse generator in 2007, at the Wayback Machine, https://web.archive.org/web/20070704002225/http://www.northgate-tech.com:80/Products/stonemanagement.asp.
Ormiston, J. A., et al., "TCT-412 non-invasive renal denervation using externally delivered focused ultrasound: early experience using Doppler based imaging tracking and targeting for treatment.", Journal of the American College of Cardiology, vol. 64, No. 11, 2014.
Owens, C. A., "Ultrasound-Enhanced Thrombolysis: EKOS EndoWave Infusion Catheter System". Seminars in Interventional Radiology, vol. 25, No. 1, Mar. 2025, pp. 37-41.
Papatsoris et al., "Update on Intracorporeal Laser Lithotripsy", Minerva Medica, vol. 104, No. 1, 2013, pp. 55-60.
Park et al., "Percutaneous Nephrolithotomy Technical Aspects," The Practical Guide to Medical and Surgical Management, 2007, pp. 621-638.
Partial File History for U.S. Appl. No. 63/154,603, filed Feb. 26, 2021.
Partial File History for Application Serial No. 63/176, 156, filed Apr. 16, 2021.
Partial File History for U.S. Appl. No. 63/193,469, filed May 26, 2021.
Partial File History for U.S. Appl. No. 63/169,091, filed Mar. 31, 2021.
Payne., "Charles Theodore Dotter: the father of intervention," Texas Heart Institute Journal, vol. 28, Issue 1, 2001, pp. 28-38.
Petition for Inter Partes Review of U.S. Pat. No. 8,728,091, filed Dec. 7, 2018.
Petition for Inter Partes Review of U.S. Pat. No. 8,956,371 Under 35 U.S.C. Section 312 and 37 C.F.R. Section 42.104, filed Dec. 7, 2018.
Petition for Inter Partes Review of U.S. Pat. No. 9,642,673 Under 35 U.S.C. Section 312 and 37 C.F.R. Section 42.104, filed Dec. 7, 2018.
Rassweiler et al. "Efficacy of in situ Extracorporeal Shock Wave Lithotripsy for Upper Ureteral Calculi" Uropean Urology, vol. 12 No. 6, 1986, pp. 377-386.
Rosenschein. et al., "Experimental Ultrasonic Angioplasty: Disruption of Atherosclerotic Plaques and Thrombi in Vitro and Arterial Recanalization in Vivo," Journal of the American College of Cardiology, vol. 15, Issue 3, 1990, pp. 711-717.
Salgaonkar, V. A. & Diederich, C. J., "Catheter-based ultrasound technology for image-guided thermal therapy: Current technology and applications." International Journal of Hyperthermia, vol. 31, No. 2, Mar. 2015, pp. 203-215.
Sasportas, L. S., et al., "Cost-effectiveness landscape analysis of treatments addressing xerostomia in patients receiving head and neck radiation therapy.", Oral surgery, oral medicine, oral pathology and oral radiology, vol. 116, No. 1, 2013, pp. e37-e51.
Scotland et al., "Stone Technology: Intracorporeal Lithotripters", World Journal of Urology, vol. 35, 2017, pp. 1347-1351.
Seshiah et al., "Novel Lithotripsy-Assisted Transcatheter Aortic Valve Replacement May Reduce Risk of Aortic Root Rupture", Journal of the Society for Cardiovascular Angiography and Interventions, vol. 2, 2023, pp. 1-4.
Shockwave C^2. "Coronary IVL System Step-by-Step Setup", Shockwave Medical, Inc., Exhibit 2163, Provided as part of case IPR2019-00405, U.S. Pat. No. 8,956,371.

(56) References Cited

OTHER PUBLICATIONS

Shockwave Medical Inc., "Shockwave Intravascular Lithotripsy (IVL) System with the Shockwave L6 Peripheral Intravascular Lithotripsy (IVL) Catheter—Instructions for use (IFU)", PN 67214-A, 2022, 6 pages.
Shockwave Medical Inc., "Shockwave Intravascular Lithotripsy (IVL) System with the Shockwave L6 Peripheral Intravascular Lithotripsy (IVL) Catheter—Instructions for use (IFU)", PN 69653-B, 2024, 5 pages.
Shockwave Medical, Investor Presentation, Slides 7-23 (Nov. 2022).
Siegel et al., "Ultrasonic plaque ablation. A new method for recanalization of partially or totally occluded arteries", Circulation, vol. 78, No. 6, Dec. 1988, pp. 1443-1448.
Sista, A. K., et al., "Applying a structured innovation process to interventional radiology: a single-center experience.", Journal of Vascular and Interventional Radiology, vol. 23, No. 4, 2012, 488-494.
Sokolov, D. L., et al., "Dual Pulse Lithotripsy Points Toward Faster, Safer Treatment for Kidney Stones", Dec. 2002, retrieved from https://acoustics.org/pressroom/httpdocs/144th/Bailey.htm, accessed on Dec. 9, 2025, 3 pages.
Sokolov, D. L., et al., "Dual-pulse lithotripter accelerates stone comminution and reduces cell injury in vitro", The Journal of the Acoustical Society of America. Vol. 112, Issue 5, Nov. 2002, p. 2290. Retrieved from https://pubs. aip.org/asa/jasa/article/112/5_Supplement/2290/541200/Dual-pulse-lithotripter-accelerates-stone, accessed Dec. 10, 2025.
Sokolov, D. L., et al., "Dual-pulse lithotripter accelerates stone fragmentation and reduces cell lysis in vitro", Ultrasound in Medicine & Biology, vol. 29, Issue 7, Jul. 2003, pp. 1045-1052.
Spratt, J.C., "Shockwave IVL Mechanism of Action" [PowerPoint Presentation], Transcatheter Cardiovascular Therapeutics Conference, San Francisco, CA, United States, Oct. 25-28, 2025.
Stoller et al., "Urinary Stone Disease: The Practical Guide to Medical and Surgical Management", 2007, 685 Pages.
Svendsen et al., "Conductance sizing balloon for measurement of peripheral artery minimal stent area," Journal of Vascular Surgery, vol. 60, No. 3, Sep. 2014, pp. 759-766.
Touya, G., et al., "Development of subsonic electrical discharges in water and measurements of the associated pressure waves", Journal of Physics D: Applied Physics, 39 (2006), pp. 5236-5244.
U.S. Appl. No. 61/289,125, filed Dec. 22, 2009.
Vorreuther et al., "Impact of Shock Wave Pattern and Cavitation Bubble Size on Tissue Damage During Ureteroscopic Electrohydraulic Lithotripsy", The Journal of Urology, vol. 153, Mar. 1995, pp. 849-853.
Vorreuther, R., et al., "Impact of voltage and capacity on the electrical and acoustic output of intracorporeal electrohydraulic lithotripsy", Urological Research, vol. 20, Sep. 1992, pp. 355-359.
Wang, Q., et al., "Effectiveness and safety of a novel IVL system for severe coronary calcification: The CALCI-CRACK trial", Canadian Journal of Cardiology, vol. 40, Issue 9, Sep. 2024, pp. 1657-1667.
Welch et al. "Laser Physics and Laser-Tissue Interaction", The Texas Heart Institute Journal, vol. 16 No. 3, 1989, pp. 141-149.
Willmann, J. K., et al., "Imaging gene expression in human mesenchymal stem cells: from small to large animals.", Radiology, vol. 252, No. 1, 2009, pp. 117-127.
Worley et al., "Electrohydraulic Shock Wave Decalcification of Stenotic Aortic Valves : Postmortem and Intraoperative Studies" Journal of the American College of Cardiology, vol. 12, Issue 2, 1988, pp. 458-462.
Yock, P. G., et al., "Teaching biomedical technology innovation as a discipline.", Science translational medicine, vol. 3, No. 92, 2011, 5 pages.
Zheng et al., "Intracorporeal Lithotripsy: Update on Technology", Urologic Clinics of North America, vol. 27, No. 2, May 2000, pp. 301-313.
Zhong et al., "Transient Oscillation of Cavitation Bubbles Near Stone Surface During Electrohydraulic Lithotripsy," Journal of Endourology, vol. 11, No. 1, pp. 55-61 (Feb. 1997).

SYSTEMS, DEVICES AND METHODS FOR GENERATING PATTERNS OF VOLTAGE PULSES AND ELECTRICAL ARCS BETWEEN SPACED-APART ELECTRODE PAIRS IN INTRAVASCULAR LITHOTRIPSY

CROSS-REFERENCE TO RELATED APPLICATIONS

This application is a continuation of U.S. patent application Ser. No. 17/449,883 filed on Oct. 4, 2021, entitled "SYSTEMS, DEVICES AND METHODS FOR GENERATING SUBSONIC PRESSURE WAVES IN INTRAVASCULAR LITHOTRIPSY," which claims priority to U.S. Provisional Patent Application Ser. No. 63/229,737, filed Aug. 5, 2021, entitled "SYSTEMS, DEVICES AND METHODS FOR GENERATING SUBSONIC PRESSURE WAVES IN INTRAVASCULAR LITHOTRIPSY," the entire contents of which applications are incorporated herein by reference.

STATEMENT REGARDING FEDERALLY SPONSORED RESEARCH OR DEVELOPMENT

None

BACKGROUND OF THE INVENTION

The invention relates to systems, devices and methods for breaking up calcified lesions in an anatomical conduit. More specifically, electrical arcs are generated between electrodes disposed within a fluid-filled balloon, creating pressure waves.

DESCRIPTION OF THE RELATED ART

A variety of techniques and instruments have been developed for use in the removal or repair of tissue in arteries and similar body passageways, including removal and/or cracking of calcified lesions within the passageway and/or formed within the wall defining the passageway. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque, often within the vessel wall. Such atheromas restrict the flow of blood, cause the vessel to be less compliant than normal, and therefore often are referred to as stenotic lesions or stenoses, the blocking material being referred to as stenotic material. If left untreated, such stenoses can cause angina, hypertension, myocardial infarction, strokes and the like.

Angioplasty, or balloon angioplasty, is an endovascular procedure to treat by widening narrowed or obstructed arteries or veins, typically to treat arterial atherosclerosis. A collapsed balloon is typically passed through a pre-positioned catheter and over a guide wire into the narrowed occlusion and then inflated to a fixed size. The balloon forces expansion of the occlusion within the vessel and the surrounding muscular wall until the occlusion yields from the radial force applied by the expanding balloon, opening up the blood vessel with a lumen inner diameter that is similar to the native vessel in the occlusion area and, thereby, improving blood flow.

The angioplasty procedure presents some risks and complications, including but not limited to: arterial rupture or other damage to the vessel wall tissue from over-inflation of the balloon catheter, the use of an inappropriately large or stiff balloon, the presence of a calcified target vessel; and/or hematoma or pseudoaneurysm formation at the access site. Generally, the pressures produced by traditional balloon angioplasty systems is in the range of 10-15 atm, but pressures may at times be higher. As described above, the primary problem with known angioplasty systems and methods is that the occlusion yields over a relatively short time period at high stress and strain rate, often resulting in damage or dissection of the conduit, e.g., blood vessel, wall tissue.

Shockwave Medical, Inc., markets an alternative to traditional relatively high pressure balloon angioplasty. The Shockwave Medical, Inc., intravascular lithotripsy system generates "shock waves" within a fluid-filled balloon. Shockwave Medical claims that generated "shock waves" travel at supersonic speed through the balloon fluid, through the balloon material to interact with the vessel wall tissue, stenosis and/or calcification. The Shockwave Medical, Inc., system requires a relatively close spacing between electrodes in an electrode pair wherein the spark gap is disposed. Shockwave Medical's currently known systems provides relatively small axial coverage of lesions. The structure of Shockwave Medical's electrode pairs thus requires additional electrode pairs spaced apart axially from each other and/or a translatable, slidable electrode pair carrier that may be used to translate the electrode pair(s) to better cover an elongated lesion.

Various embodiments of the present invention address these issues, among others, discussed above.

BRIEF DESCRIPTION OF THE SEVERAL VIEWS OF THE DRAWINGS

These drawings are exemplary illustrations of certain embodiments and, as such, are not intended to limit the disclosure.

DETAILED DESCRIPTION OF THE INVENTION

Figure 1:
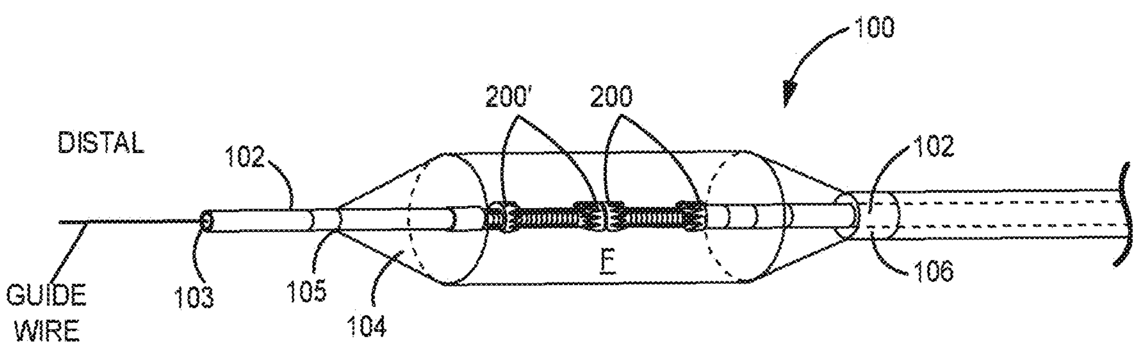
FIG. 1 illustrates a perspective and partial cutaway view of a distal region of one embodiment of the present invention.

Generally, embodiments of the present invention comprises methods and devices for generating subsonic waves for disrupting or cracking calcified regions within a blood vessel, though the disruptive effects of the generated subsonic waves may extend to partially or non-calcified occluding material. More specifically, with reference to the Figures, an exemplary embodiment 100 comprises an elongated member or carrier 102 such as a catheter with a known inflatable angioplasty balloon 104 mounted on or near the distal end 103 of the elongated carrier 102 which in certain embodiments may comprise a laser cut polyimide tube. The distal end 105 of the balloon 104 may be sealed against or around the elongated carrier 102 to create a watertight barrier and further comprises a fluid inflating/deflating channel 106 in fluid communication with the interior of the balloon 104 and in fluid communication with a fluid-containing reservoir (not shown) that is located external to the patient, and as is well-known in the art, for inflating the balloon 104 with fluid F and deflating balloon 104. A guide wire lumen (not shown but as is well-known in the art) configured to allow translation of a guide wire extends through the elongated carrier and distally out therefrom, an arrangement also well known to the skilled artisan.

It is to be understood that the various embodiments of the present invention are also effective within a fluid-filled environment, e.g., a bodily cavity and/or a blood vessel, i.e., without requiring a fluid-filled balloon. The various embodiments are described in relation to a fluid-filled balloon, but will also apply to an elongated catheter disposed within a fluid-filled environment wherein the subsonic pressure wave generators described infra may be disposed along the elongated carrier within the fluid-filled environment. All such embodiments are within the scope of the present invention.

Therefore, at least one subsonic pressure wave generator 200 is provided, wherein each subsonic pressure wave generator comprises a proximal ring electrode and a distal ring electrode, with a spark gap defined therebetween. In some embodiments, two subsonic pressure wave generators 200, 200' may be provided. In still other embodiments, more than one subsonic pressure wave generator, i.e., two or more, may be provided.

As referred to herein, subsonic pressure wave generator is defined as a mechanism that, when actuated, generates a wave(s) of energy within a fluid-filled environment such as an angioplasty balloon. The generated wave(s) thus travel through the balloon material at subsonic speed and also interact with tissue and/or calcified material located outside of the balloon at subsonic speed. In other words, the wave(s) generated by the subsonic pressure wave generators do not travel through the balloon material or impact tissue or calcified material outside of the balloon at the speed of sound or greater. Further, the term "wave" is not intended to be limiting to a "wave" per se. Instead, a traveling front of energy is generated and that moves through the fluid within the balloon, generally away from the subsonic pressure wave generator from which it emanates. This traveling front of energy may comprise a symmetrical expansion shape around the elongated catheter 102, or may expand and travel in an asymmetric shape relative to the elongated catheter 102. In each embodiment, the traveling front of energy, i.e., the "wave" as referred to herein, travels through the balloon material and impacts materials outside of the balloon at subsonic speeds.

Alternatively, the subsonic pressure wave generator may comprise a resistive heater or a pulse heater as is known in the art.

If a single subsonic pressure wave generator 200 is provided, it may be substantially axially centered within the balloon 104. In other embodiments, the single subsonic pressure wave generator 200 may be biased to the proximal or to the distal end of the balloon's interior.

When two or more subsonic pressure wave generators are provided, 200, 200', adjacent subsonic pressure wave generators, e.g., 200, 200', may be spaced axially apart from each other, wherein the resultant spark gaps defined by each subsonic pressure wave generator 200, 200', are axially spaced apart from each other. In cases wherein three or more subsonic pressure wave generators are provided, the resultant spark gap between adjacent subsonic pressure wave generators may be substantially equal, or one or more spark gaps may be longer or shorter than other subsonic pressure wave generators.

As further seen in the Figures, a first, proximal, subsonic pressure wave generator 200 may comprise a proximal ring electrode 201 and an axially spaced apart distal ring electrode 202, defining a spark gap therebetween. Next, a second, more distal, subsonic pressure wave generator 200' may comprise a proximal ring electrode 203 and an axially spaced apart distal ring electrode 204, also defining a spark gap therebetween. As will be discussed further, the distal ring electrode 202 of subsonic pressure wave generator 200 and the proximal ring electrode 203 of subsonic pressure wave generator 200' may be in electrical communication with each other to enable current to flow therebetween.

As will be understood by skilled artisan, the electrical communication may be effectively reversed. First, e.g., with a proximal electrode electrically coupled or in electrical communication with a "high" power side of a circuit and pulse generator connected therein, and a distal electrode electrically coupled or in electrical communication with a "ground" or "return" side of the circuit and pulse generator connected therein. Second, a distal electrode may be electrically coupled or in electrical communication with a "high" power side of a circuit and pulse generator while a proximal electrode may be electrically coupled or in electrical communication with a ground or return side of the circuit and pulse generator. In either case, once the subsonic pressure wave generator(s) is/are actuated, the circuit is completed and current will flow through the circuit.

At least one of the subsonic pressure wave generators, e.g., 200 may be in direct electrical connection and communication with an externally located power source or pulse generator 300, wherein the pulse generator may be configured to provide voltage pulses of a predetermined magnitude and pulse length along an electrical conductor to a proximal ring electrode of a proximal-most subsonic pressure wave generator 200. Alternatively, the voltage pulses may be delivered without a predetermined magnitude or pulse length. In some embodiments, a collapsing field in an inductor, e.g., a well-known car ignition mechanism), or decaying voltage from a capacitor may be employed, neither of which comprise or require a predetermined voltage or pulse length.

Each subsonic pressure wave generator 200, 200', etc., comprises a pair of axially spaced-apart ring electrodes. Electrode pairs 201, 202 and 203, 204 are shown in axially spaced-apart disposition and mounted around the elongated carrier 102, e.g., by crimping or other attachment means and are immersed within the fluid F in the inflated balloon 104. Accordingly, spark gaps are defined between electrode pair 201 and 202, and between electrode pair 203 and 204, wherein electrodes 202 and 203 are in operative electrical communication or connection. As discussed above, the spark gaps may be of equivalent length or may comprise differing lengths. In some embodiments, a single subsonic pressure wave generator 200 may be provided, while in other embodiments, more than one subsonic pressure wave generator 200, 200', etc., may be provided.

Thus, in some embodiments, first and proximal-most ring electrode 201 may be electrically coupled or in electrical communication or connection, via an electrical conductor, with a power source, e.g., the pulse generator 300, that is configured for supplying voltage pulses to the electrode pair(s) comprising the subsonic pressure wave generator(s) 200. The distal-most ring electrode, e.g., 204, may also be electrically coupled or in electrical communication or connection, via a second electrical conductor, with the power source, e.g., pulse generator 300.

The fluid F within the inflated balloon 104 is ionically conductive, e.g., saline, to facilitate arcs, or current flow, between the spaced-apart ring electrodes in each electrode pair 201, 202 and 203, 204 comprising the subsonic pressure wave generators 200 and 200'. Thus, upon application of sufficient voltage generated by the pulse generator 300 to the proximal-most electrode, e.g., 201, via a conductor in electrical connection or communication between pulse generator 300 and electrode 201, may cause current to flow between electrode 201 and electrode 202 and wherein an arc is generated across the defined spark gap between electrodes 201, 202. A return conductor in operative electrical connection or communication with electrode 202 completes the circuit back to the pulse generator 300. In this manner, the circuit may complete or close during the arcing between ring electrodes 201, 202 in an embodiment having a single electrode pair comprising a single subsonic pressure wave generator 200.

It is known that current can flow between the electrodes without an arc. Current generally flows in an electrolyte by ion diffusion. An arc or spark is present when electrons or ions can accelerate past the ionization energies of the local molecule, creating a cascade. Often, this is a plasma and may occur through the bulk fluid, e.g., the conducting fluid F, but is more likely to occur along a fluid-surface interface, e.g., along the outer surface of the catheter 102. These conditions may also result in generation of subsonic pressure waves as described above.

In an embodiment comprising more than one subsonic pressure wave generator 200, 200' such as illustrated, upon application of sufficient voltage by the pulse generator 300, the current flow (arcing) may proceed from electrode 201 to electrode 202 across the defined spark gap therebetween. Next, electrode 202, being in operative electrical communication with electrode 203, enables current to flow from electrode 202 to electrode 203 which, in turn, results in current flow from electrode 203 to electrode 204, across the spark gap defined therebetween. A return conductor in operative communication with electrode 204 completes the circuit back to the pulse generator 300.

The flow discussed above comprises a "current" passing from electrode 201 to 202 is initially ion diffusion as discussed above (before the arc is established), followed by streamers initiating from one or more points 206 of electrode 201, followed by plasma channels being formed either through the fluid F and/or at, or along, the fluid F surface interface. The fluid F surface interface may comprise the outer surface of catheter 102 and/or the inner surface of angioplasty balloon 104.

Figure 6:
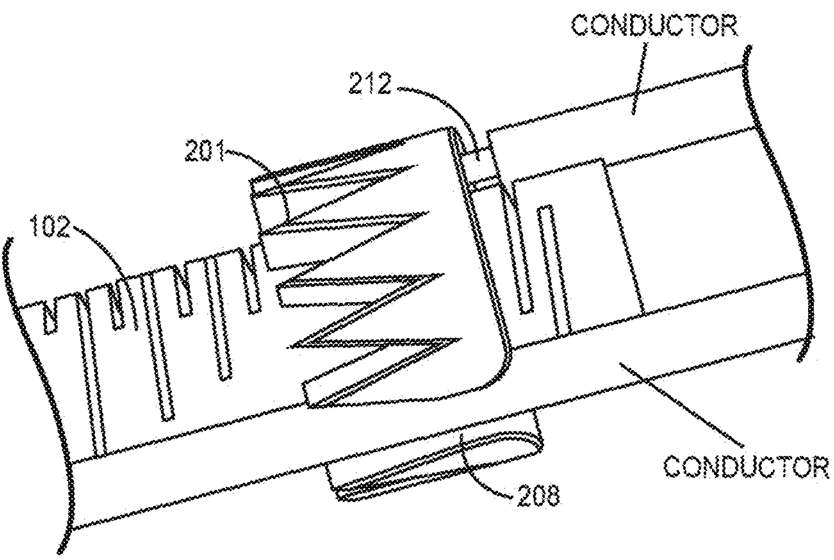
FIG. 6 illustrates a side cutaway view of a portion of a distal region of one embodiment of the present invention.
Figure 7:
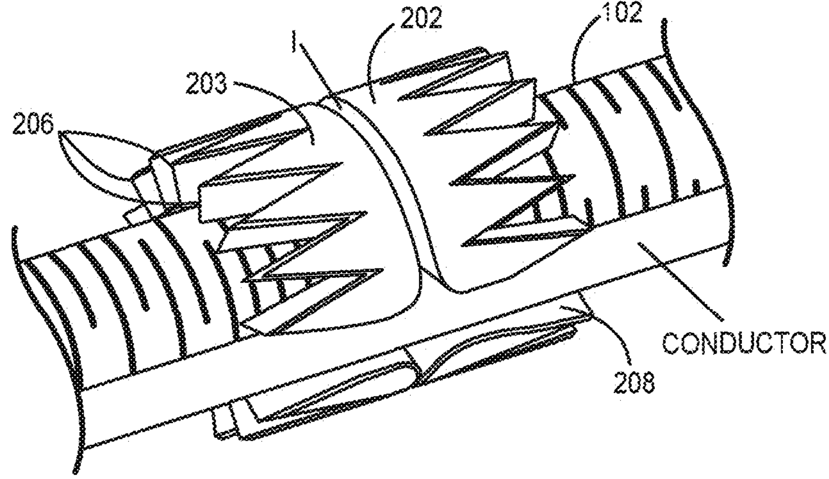
FIG. 7 illustrates a perspective, cutaway view of a portion of a distal region of one embodiment of the present invention.

FIG. 1 illustrates the fluid-filled balloon 104 in an inflated state wherein a conductive fluid F such as saline fills the balloon's interior space, with the spaced-apart ring electrodes 201, 202 and 203, 204 disposed therein and immersed in fluid F. Electrodes 201, 202, 203 and 204 are arranged generally symmetrically around the elongated carrier 102 and generally symmetrically along a center line of the inflated balloon 104. However, in a preferred embodiment, as shown in at least FIG. 6, a channel 208 may be defined through or along the ring electrodes along a longitudinal plane to allow the insulated conductor(s) to be disposed at least partially therein so as to reduce crossing profile of the system. Thus, the channel 208 may be formed by carving out a portion of ring electrode wherein the ring electrode does extend circumferentially around the elongated carrier 102. Alternatively, as illustrated in FIG. 6, channel 208 may comprise a void or space between two spaced-apart ends of the ring electrode, wherein the ring electrode extends partially circumferentially around the elongated carrier 102 and wherein the conductor may extend along the outer surface of elongated carrier 102. With the exception of the interruption of the channel 208 in the ring electrode(s), the preferred structure is symmetrical as discussed above, though asymmetrical electrode(s) may also be employed.

FIGS. 2-12 illustrate possible arrangements and embodiments of the spaced-apart ring electrodes that form each electrode pair as well as the conductive wire connections thereto.

Figure 2:
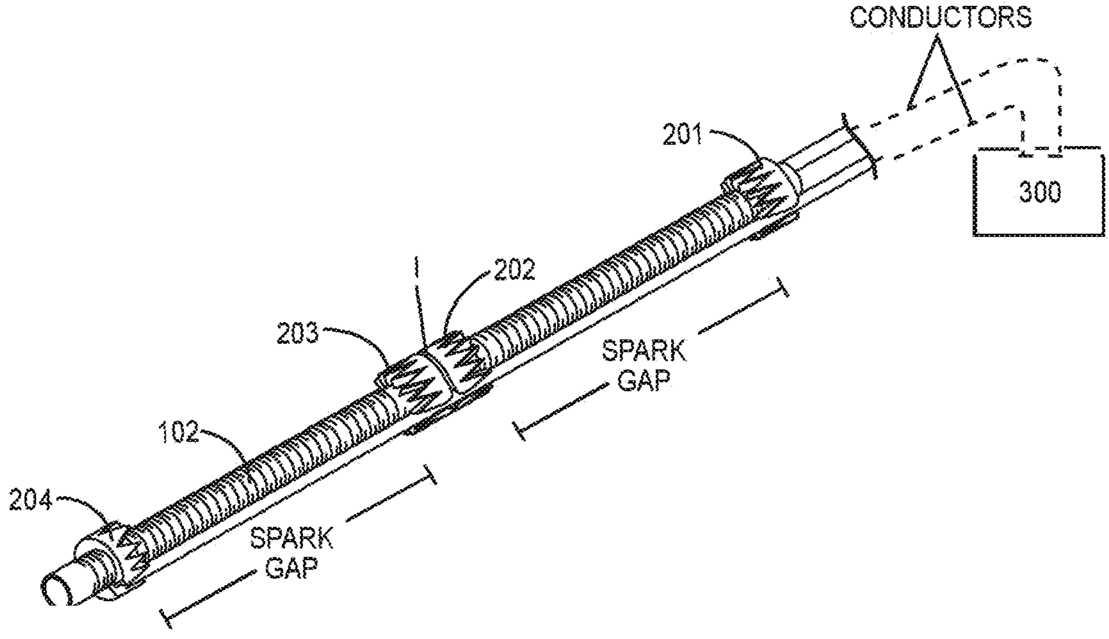
FIG. 2 illustrates a perspective view of a distal region of one embodiment of the present invention.
Figure 3:
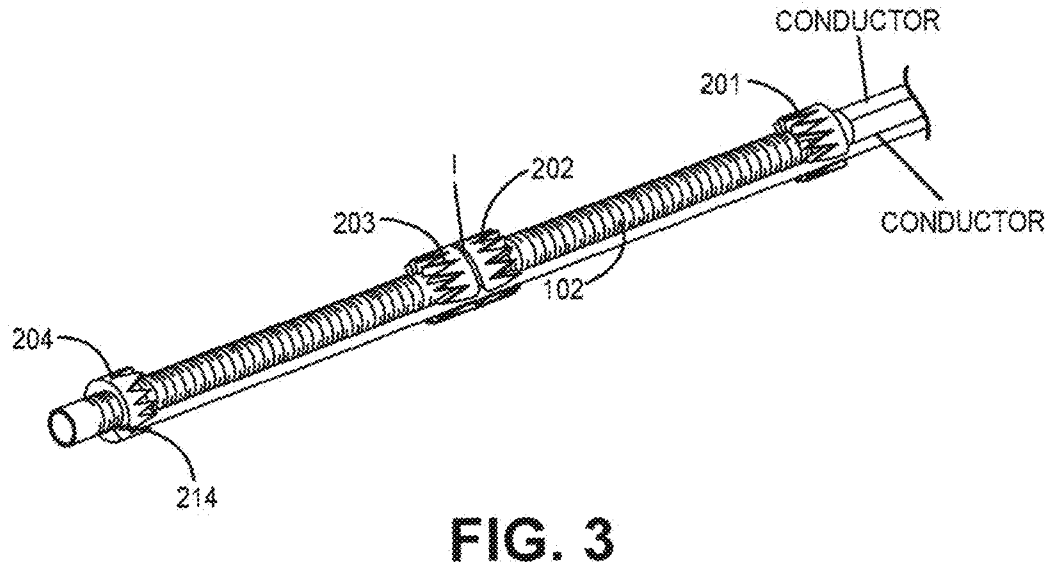
FIG. 3 illustrates a perspective view of a distal region of one embodiment of the present invention.

FIG. 2 thus illustrates the elongated carrier 102, which may comprise a laser cut tube and may comprise polyimide or other material. Two exemplary subsonic pressure wave generators 200, 200' are shown in axially spaced-apart relation relative to each other along the elongated carrier 102. Each subsonic pressure wave generator, e.g., 200, 200', comprise spaced-apart exemplary ring electrodes, respectively 201, 202 and 203, 204, each defining a spark gap between the relevant spaced-apart ring electrodes of a predetermined length, that is the spacing distance between the spaced-apart ring electrodes 201 to 202, and 203 to 204. The distal ring electrode, e.g., 202, of the proximal subsonic pressure wave generator 200 and the proximal ring electrode 203 of the distal subsonic pressure wave generator 200' are shown in relatively close disposition forming an interface I therebetween, the interface defining and comprising an electrical communication between the two ring electrodes defining the interface I.

The various forms and types of electrical connections between these intermediary ring electrodes 202, 203 defining an interface I are described further herein, but generally comprise a physical or operative electrical connection between surfaces of the two intermediary ring electrodes that may comprise a touching relationship, a weld bead, or a jumper wire or other conductive interconnection element, or mechanism, between the two intermediary ring electrodes 202, 203, or other conducting connection. The skilled artisan will readily recognize alternative mechanisms for creating the required electrical connection between the intermediary ring electrodes, 202, 203 i.e., between adjacent subsonic pressure wave generators 200, 200', each of which is within the scope of the present invention. In this arrangement, the two or more subsonic pressure wave generators 200, 200', etc., may be electrically connected in what effectively becomes a series circuit. The number of subsonic pressure wave generators used in certain embodiments may be one, or two, or more than two.

As discussed further herein, the ring electrodes described herein are exemplary, other electrodes shapes and structures are within the scope of the present invention. In certain embodiments, and as discussed further infra, at least one of the electrodes in an electrode pair comprising a subsonic pressure wave generator may comprise a plurality of points or extensions that extend toward the spark gap defined between the electrode pair.

Still further, certain embodiments may comprise a plurality of electrode pairs, at least one electrode pair comprising a proximal-most ring electrode in wired, or other, electrical communication with the pulse generator 300. In some embodiments, more than one electrode pair in the plurality may comprise a proximal-most ring electrode in wired, or other, electrical communication with the pulse generator 300, wherein at least one of the electrode pairs in the plurality may be separately and individually energized by the pulse generator 300. Thus, certain embodiments may comprise a parallel connection arrangement of at least some electrode pairs, or may comprise a combination of series connected sets of electrode pairs with one or more sets of electrode pairs comprising a parallel connection back to pulse generator.

The skilled artisan will recognize that the reference to an operative electrical connection or communication with a proximal-most ring electrode of an electrode pair and the pulse generator 300 is merely illustrative. It is within the scope of the present invention to simply switch the operative electrical connection to be between a distal-most ring electrode of an electrode pair and the pulse generator 300.

In certain configurations, individual subsonic pressure wave generators, 200, 200' may be controlled regarding the magnitude of voltage applied, the magnitude of current flow resulting in an arc between the ring electrodes comprising the subsonic pressure wave generators, the time duration of current flow and arcing between the ring electrodes comprising the subsonic pressure wave generators, the current in the primary of a discharge inductor, the charge in a discharge capacitor and/or the initiation time of the current flow or arcing between the ring electrodes comprising the subsonic pressure wave generators.

Figure 13:
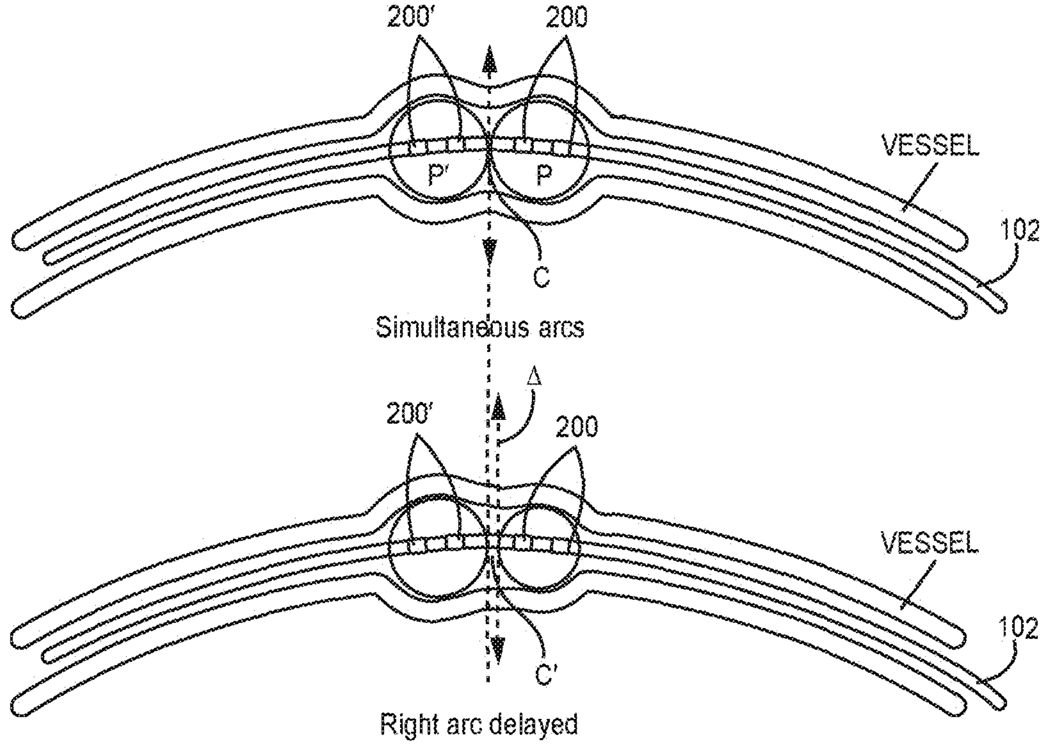
FIG. 13 illustrates a side view of simultaneous arcs and a side view with one arc delayed relative to the other arc.

For example, and with reference now to FIG. 13 and application of the related detailed description infra, is possible to axially translate or shift a central node between generated pressure waves by slightly delaying generation of one pressure wave by one or more adjacent subsonic pressure wave generators, e.g., 200 or 200', relative to the timing of generation of a pressure wave by an adjacent subsonic pressure wave generator, such variable gap spacing may also provide an alternative, or supplemental, mechanism for moving the resulting pressure waves, and nodes disposed therebetween, axially along the catheter 102 within balloon 104. The delay in pressure wave generation may be used alone, or in combination with the axial spacing differentials between adjacent subsonic pressure wave generators 200, 200'.

As shown in FIG. 13, two (or more) pairs of ring electrodes, 201/202 and 203/204 may be provided within the fluid-filled balloon. The arcing for each pair 201/202 and 203/204 may be generated substantially simultaneously, resulting in equal-sized bubbles at any given time and subsonic pressure waves P with a central node C generally in the middle of the generated subsonic pressure waves P.

Alternatively, one arc (and resultant subsonic pressure wave P) may be slightly delayed which is used to shift the central node C proximally or distally to enable treating along the axial length of the balloon. FIG. 13 illustrates the axial offset A of the central node C vs C' as a result of this delay technique. Such a delay in arcing, and resulting subsonic pressure wave P' which is slightly delayed relative to subsonic pressure wave P, may be timed and used to create a sweeping effect of a axially translating pressure wave through the length of the balloon and along the length of the lesion. A processor may be provided as well-known in the art to execute a pre-programmed set of instructions comprising various timing sequences of the pulses and resulting arcs and pressure waves to optimize focus of the waves including, but not limited to sweeping the lesion in axial directions. As shown, the pairs of interacting ring electrodes 201/202 and 203/204 are adjacent each other along the elongated carrier. In other embodiments, non-adjacent ring electrode pairs may interact as discussed above.

Catheter and Electrodes

As provided above, an exemplary laser-etched polyimide tube 102 may be provided with ring electrodes 201, 202 and 203, 204, wherein the ring electrodes are crimped around the tube, with insulated wires connecting the ring electrodes back to the external pulse generator 300.

In the two-wire configuration shown, the gap between the electrodes may be decreased by opening the distance between the two adjacent center, intermediary electrodes (202 and 203) in the electrode pairs while electrically connecting them with an additional wire.

Figure 9:
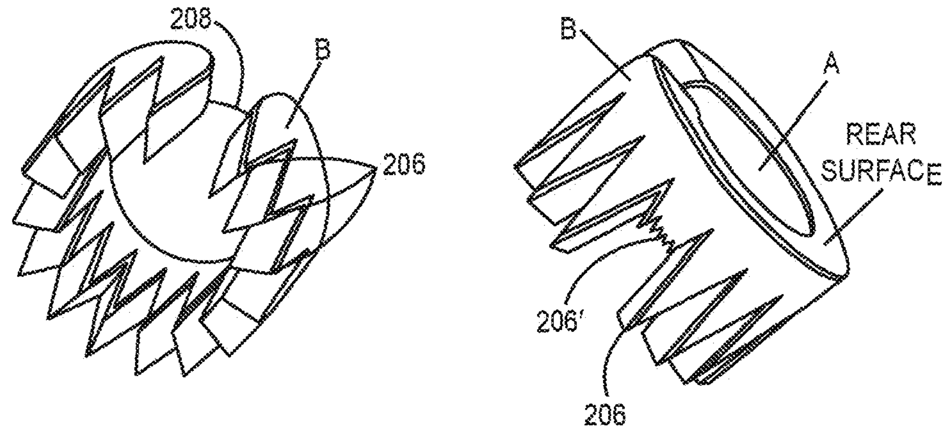
FIG. 9 illustrates perspective views of ring electrodes of one embodiment of the present invention.
Figure 10:
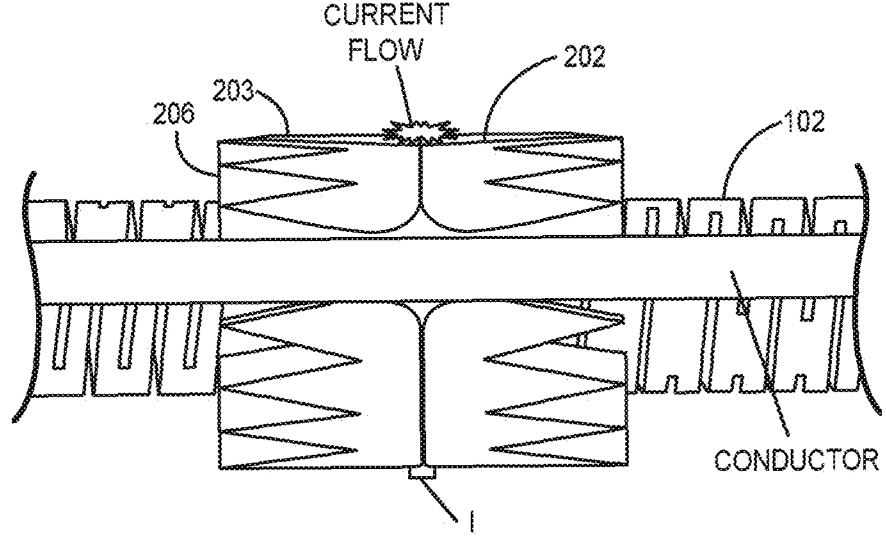
FIG. 10 illustrates a side cutaway view of two intermediary electrodes with an operative electrical communication therebetween.

FIG. 9 provides an exemplary ring electrode E having a body portion B defining a central aperture A configured to securely engage the catheter 102, channel 208, a front surface defining a plurality of points 206 and a flat rear surface. Points 206' illustrate exemplary effects of corrosion on one of the points caused by arcing between adjacent ring electrodes. One or more of the remaining points 206 may engage to generate the arc across the spark gap.

The points 206 may comprise a substantially triangular profile as illustrated. However, other profiles are also contemplated. The underlying functionality of the points 206 is to enable arcs to initiate from different locations on the electrode. Therefore, any shape that extends away from the main body of the electrode generally toward the distal-most electrode in an electrode pair, and generally toward the spark gap defined therebetween, comprising a subsonic pressure wave generator will be sufficient. The tip regions of adjacent ones of the plurality of points are in certain embodiments, spaced apart from each other.

Multiple points 206 on the exemplary ring electrodes facing the spark gap region defined between ring electrodes, e.g., 201, 202, allow electrical breakdown streamers to initiate from several different locations or points 206 disposed on and/or around the ring electrode, so viable points 206 remain when some are corroded by the arc. This extends the effectiveness and life of the ring electrode. In addition, the path of the arc may comprise debris, so originating arcs from different locations, i.e., points 206, on the electrode(s) aids in reducing the debris, making it less likely that a short is formed. In this way, the environment surrounding the electrodes and within the spark gap therebetween is maintained as uniformly as possible throughout the treatment session comprising a plurality of pulses.

Figure 5:
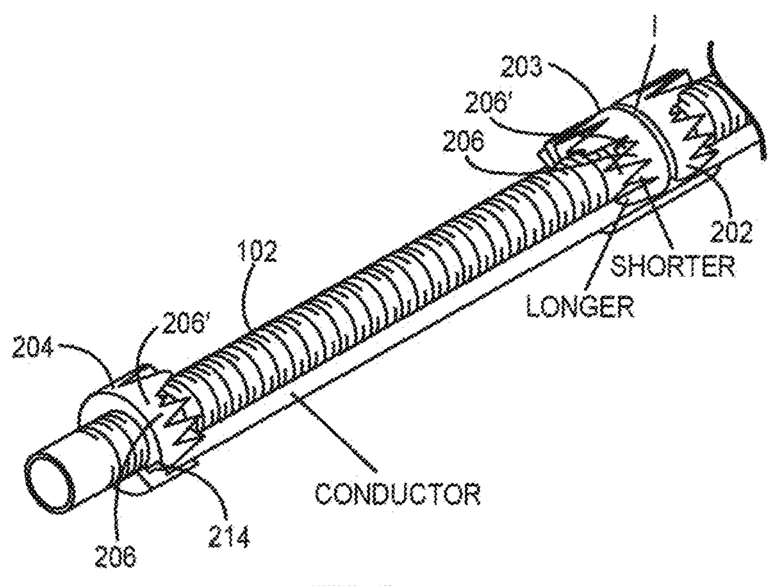
FIG. 5 illustrates a perspective, cutaway view of a portion of a distal region of one embodiment of the present invention.

Accordingly, as illustrated in the Figures, and as the skilled artisan will readily understand, the uncorroded point (s) 206 involved in electrical arcs, begin to corrode as electrical arcing proceeds. As shown in FIGS. 5 and 9, points 206 corrode to shorten to form degraded or corroded points 206'. In turn, as will be understood and illustrated, the spark gap between corroding, or corroded, points 206' will lengthen, creating a greater length of fluid and distance, and resistance, therebetween. Thus, the current flow streamers may continually seek out a shorter, less resistant, spark gap formed or defined by, or between one or more uncorroded points 206 that are longer in length that corroded point(s) 206'. Relatedly, in some embodiments, as best shown in FIG. 5, one or more of the uncorroded points 206 may have a length that is longer than one or more of the other points 206, as measured by the point(s) 206 relative length of extension toward the spark gap. The longer point(s) 206 thus comprise a spark gap length that is shorter, and less resistant, than the spark gap length of other point(s) 206 that are shorter, or the spark gap length of points 206' that are corroded and, therefore, shortened to define a longer spark gap length therebetween. FIG. 5 shows an exemplary set of points 206 wherein one point 206 is "longer" than an adjacent "shorter" point 206 and a still shorter point 206' that has been shortened by corrosion by electrical arcing. As the skilled artisan will readily understand, current flow streamers may preferably seek out a shorter, less resistant, spark gap, i.e., a spark gap comprising one or more "longer" points 206.

The electrodes, including exemplary ring electrodes 201, 202, 203, 204, may be metal or semiconductor, and can be plated with a secondary alloy. The base metal may comprise copper or beryllium copper. The plating may comprise platinum, gold, tungsten, osmium, silver, nickel, or other electrochemically low-activity metal. Carbon surfaces such as graphite, graphene, and diamond may also be used. Still further, stainless steel and steel alloys may be used.

The connection between electrode pairs, e.g., 201, 202 and 203, 204, may be achieved in many embodiments. As discussed above and as shown in FIG. 10, in one embodiment, the two intermediary ring electrodes, e.g., 202 and 203, may be placed in a physically touching relationship wherein the electrical connection effectively comprises a short between the touching electrodes 202, 203, allowing current to flow therebetween. The electrode rings 201, 202, 203, 204 may comprise a rear surface (shown in FIG. 9) that may be substantially flattened, wherein the rear surfaces of intermediary ring electrodes 202, 203 may be in a physically touching engagement. Alternatively, the rear surfaces of exemplary intermediary ring electrodes 202, 203 may be spaced apart as further discussed here. Still more alternatively, the rear surfaces of the intermediary ring electrodes may comprise complementary shapes, e.g., one convex and the other concave, wherein one rear surface fits within the other rear surface to comprise a fuller physically touching engagement between the intermediary ring electrodes, e.g., 202, 203. The rear surface which may be relatively flattened comprises the side opposite the plurality of points 206 which form and define a front surface of each exemplary ring electrode 201, 202, 203 and 204.

Figure 11:
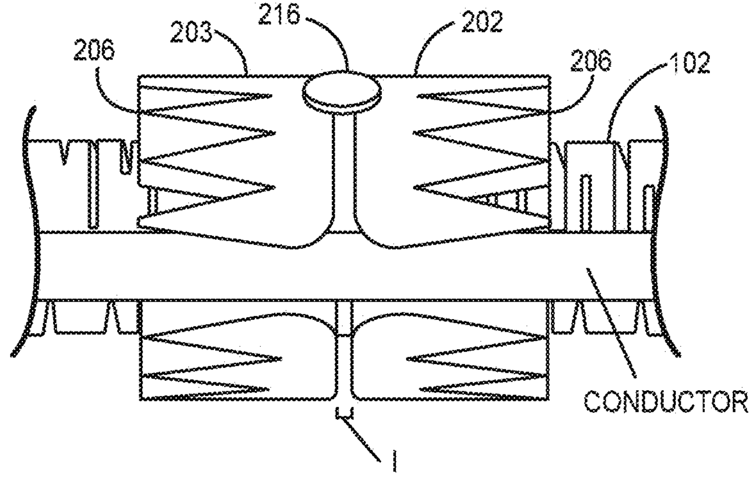
FIG. 11 illustrates a side cutaway view of two intermediary electrodes with an operative electrical communication therebetween.
Figure 12:
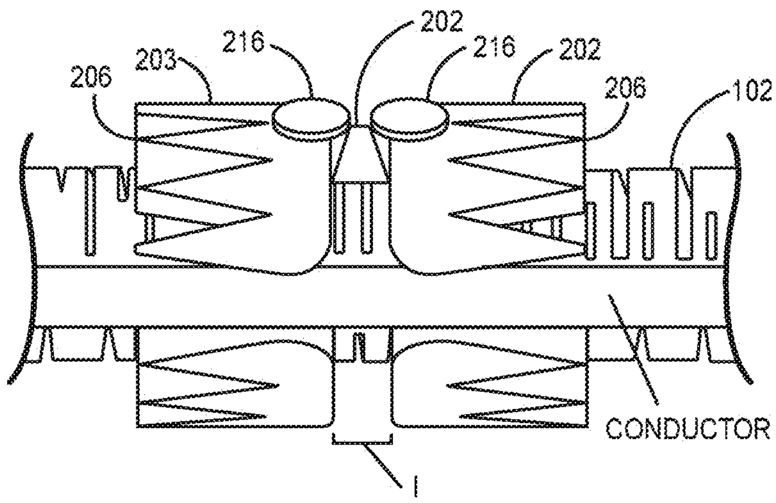
FIG. 12 illustrates a side cutaway view of two intermediary electrodes with an operative electrical communication therebetween.

As shown in FIG. 12, rear surfaces of intermediary electrodes 202, 203 may be configured in an adjacent but spaced, apart and non-touching engagement, wherein a jumper conductive wire is disposed between the intermediary electrodes 202, 203 across interface I, or, as in FIG. 11, a welded bead interconnects the electrodes 202, 203 at the interface I. Alternative means to achieve the required electrical connection at the interface I between intermediary ring electrodes 202, 203 may appear to the skilled artisan, each such electrical connection means is within the scope of the present invention.

Alternative electrode embodiments comprise at least some non-ring electrodes attached or mounted or connected with the elongated catheter 102, wherein pairs of the non-ring electrodes are arranged in spaced-apart configurations to form subsonic pressure wave generators as described above in connection with the ring electrode embodiments. Ring and non-ring electrodes may be combined in a given system.

Still more alternatively, at least some of the electrodes may be disposed along the inner surface of the balloon 104. In certain embodiments a proximal electrode, e.g., a ring electrode such as 201 may be provided and mounted on or along catheter 102, and paired with an electrode disposed along the inner surface of balloon 104. As voltage pulses are applied, an arc may generate between the catheter-mounted electrode and the balloon-mounted electrode, generating in turn subsonic pressure wave(s). Still further, a distal catheter-mounted electrode, e.g., ring electrode 202, may be spaced away from both the proximal catheter-mounted electrode and from the balloon-mounted electrode. In this embodiment, a first subsonic pressure wave may result from an arc between the proximal catheter-mounted electrode and the balloon-mounted electrode. A second subsonic pressure wave may then result from an arc between the balloon-mounted electrode and the distal catheter-mounted electrode. A heat shield may be disposed along and/or around the region where the balloon-mounted electrode is positioned to aid in heat dissipation and conduction of generated heat away from the balloon material.

Finally, the subsonic pressure wave generators may all be mounted along the inner surface of the balloon, with arcs and resulting subsonic pressure wave generation as described herein.

Electrodes mounted on the inner balloon surface may comprise a carbon filament in operative communication with a pulse generator and which may also affect, e.g., limit, the expansion radius of the balloon.

In all of the cases, a plurality of points 206 may be provided on at least one of the electrodes in an electrode pair comprising a subsonic pressure wave generator.

The plurality of points 206 will also help in cases where the elongated catheter 102 is in a curved disposition due to the tortuosity of the subject vessel. In this situation, the points 206 of the subject electrodes in an electrode pair that are on an inner radius of the curved catheter 102 are in closer proximity to each other than the points 206 on an outer or intermediary radius. Thus, these points 206 that are in closer/closest proximity will be likely to generate the arc and resultant subsonic pressure wave.

Further, it is possible to create a preformed curvature in the catheter 102 in order to effectively select which points 206 are likely to generate the arc and resulting subsonic pressure wave. Such a preformed curvature may be built into the catheter 102 using a mandrel and heat setting or other known techniques and/or shaping metal alloys such as Nitinol. One of more of these preformed curvature region(s) may be located along the section inside the balloon 104. This deformation or curvature may be straightened by translation over the guide wire, and subsequent withdrawal of the guide wire allows the subject preformed curvature region to successively move from a deformed straightened configuration to a non-deformed and curved configuration. As will now be apparent, more than one of these preformed curved regions may be provided within the balloon and may be positioned adjacent to electrodes, within or along electrode pairs and/or subsonic pressure wave generators. The preformed curved regions may take curved excursion paths that are in a same direction, or in different directions and may be interposed with straight non-curved sections. In this way, the operator may effectively change the direction of the pressure wave to create more effective disruption of the targeted region.

In certain embodiments, individual points 206 may be specifically energized with individual wired connection(s) and/or individual points 206 may be de-energized in order to ensure they do not participate in current flow, for at least a period of time and/or during treatment of a certain region of the subject vessel.

In other embodiments, the points 206 may be selectively and intentionally degraded (or not degraded) based on material selection and/or relative length of the tip of certain of the points 206 relative to the other points 206.

Wiring/Cabling

The disposable catheter assembly may comprise two or more insulated conductors connecting the system of electrodes, electrode pair(s) and/or subsonic pressure wave generator(s) to the power supply. A typical excitation pulse is 50 A @ 2 KV for 5 usec, requiring a load impedance of 40 ohms. The round trip cable length in the disposable catheter is approximately 10 feet, so the maximum resistance of the cable is 2 ohms/foot for each trace.

Twisted wire pairs may form transmission lines whose characteristics change with the wire diameter and spacing. If, for example, 40 ga copper wire is spaced 0.25 mm (10 mils) apart (for 5 mil thick insulation), the twisted wire pair may form a 1.1 uH inductor which may, in turn, cause the rise time of an ideal 50 A 2 KV source to be about 25 nsec. Alternatively, larger, more conductive wire may be used and a resistance may be added to the circuit to accommodate the ideal resistance in the system.

Figure 4:
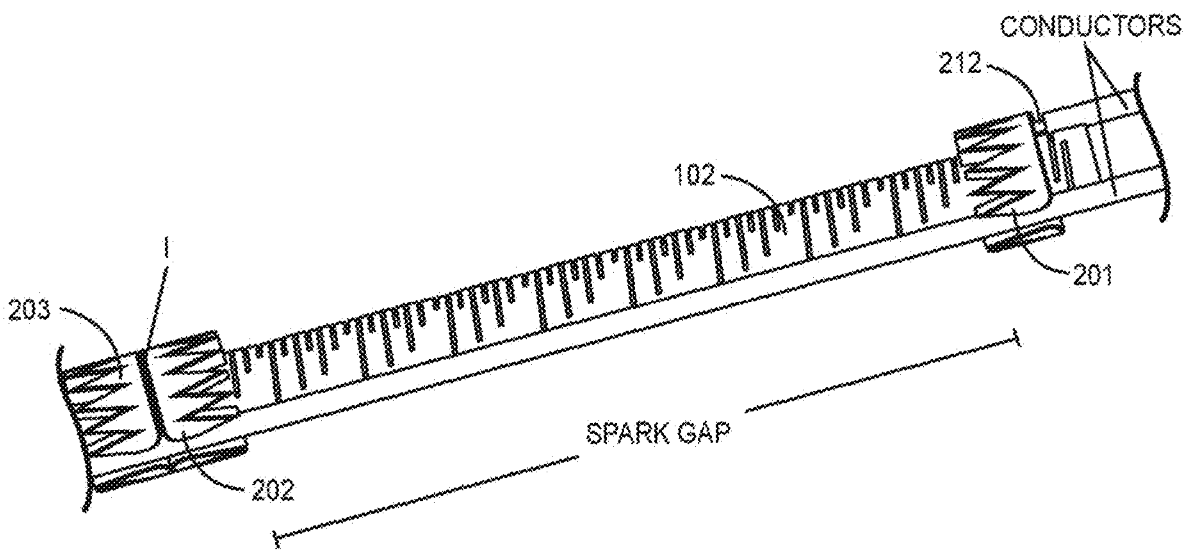
FIG. 4 illustrates a side, cutaway view of a distal region of one embodiment of the present invention.

The Figures illustrate electrical conductors comprising insulation that are operatively connected with the pulse generator 300 and wherein one of the electrical conductors is in electrical communication with the proximal-most ring electrode 201, an electrical structure well-known to the artisan. FIG. 4 provides an exemplary connection embodiment wherein a distal end of conductor is stripped of insulation exposing a length of distal conductor portion 212 that is operatively connected with ring electrode 201. A similar connection mechanism may be employed for the connection between the other electrical conductor and the distal-most ring electrode, e.g., element 204.

Figure 8:
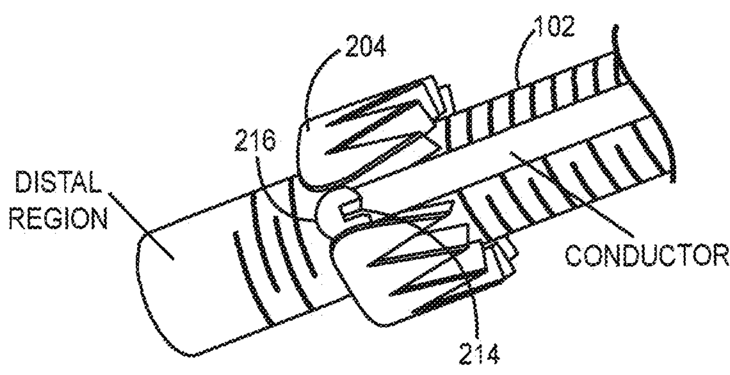
FIG. 8 illustrates a perspective, cutaway view of a portion of a distal region of one embodiment of the present invention.

Alternatively, a conductor may comprise a distal conductor portion 214 that is stripped of insulation and that is connected with the relevant ring electrode by a weld bead 216 as shown in FIG. 8. Any of the electrical conductors may be connected to the relevant ring electrode in this manner.

In order to minimize outer diameter and crossing profile of the system, the electrical conductors may be run within a lumen defined in catheter 102, wherein the distal conductor portion is operatively connected with the relevant ring electrode through an aperture in the catheter 102 and/or via a weld bead as described above.

Alternatively and as shown in the Figures, the ring electrodes 201, 202, 203, 204, may comprise a channel 208 sized for the electrical conductor(s) to reside within. The channel 208 may provide the connection point for one or more of the ring electrodes as is shown in, e.g., FIG. 8. Channel 208 may allow the electrical conductor(s) to slide there along to accommodate changes in the attitude of the catheter 102 during advancement of the device 100 through a patient's vasculature.

Still more alternatively, a longitudinal channel or a spiral or other shaped channel may be defined in the wall of elongated catheter 102. The conductor(s) may be at least partially disposed in the channel to assist in minimizing crossing profile of the system.

Power Supply/Pulse Generator

In some embodiments, a capacitor bank may be provided and may be charged during an exemplary 1-minute off period, followed by a short or connection of the capacitors to the electrodes for the discharge and arc generation. The charging period may be less than 1-minute in preferred embodiments. In other embodiments, a current may be established in a transformer primary, wherein that current is halted to generate a large voltage across the secondary.

As noted, the charging period may be much less than 1 minute as a pulse may be delivered to the electrodes at least once a second. The pulse rate may be limited with sensed temperature of the conductive fluid F and/or balloon material so that the temperature of surrounding tissue is not increased beyond a predetermined threshold, e.g., 1 degree C. of temperature increase for cardiac tissue. The temperature may be monitored using a temperature sensor mounted along the outside surface of the catheter 102 within the conductive fluid F and/or on an inner surface of the balloon, or other location. The temperature sensor may be in operative communication with an externally located processor having operational communication with the predetermined heat threshold(s) and wherein an alert is provided via a display or other mean. In some embodiments, the voltage pulses may be locked out, with no further pulses allowed. In other embodiments, no further voltage pulses are allowed when the predetermined heat threshold is met or exceeded, but the voltage pulses may proceed when the sensed temperature drops below the predetermined heat threshold.

The capacitor bank may be charged from either direction and FETs are controlled to allow the capacitor banks to discharge between the electrodes in an H-bridge configuration. In some embodiments, the current sign may be configured to flip. Phase shaping may be executed to reduce EMI in some embodiments. In some embodiments, both the current and voltage may be monitored to inform what the voltage setting should be for the next pulse delivery. In some embodiments, the voltage may be terminated on a pulse-by-pulse basis and in other embodiments the voltage is not terminated on a pulse-by-pulse basis. Similarly, the electrical arc across a given set of electrodes comprising a subsonic pressure wave generator may be terminated on a pulse-by-pulse basis in some embodiments, while in other embodiments, said electrical arc may not be terminated on a pulse-by-pulse basis.

Because the treatment scales with the cube root of the deposited energy, casual control of voltage and current suffices. The current may flip sign between pulses, droop or exponentially decay during the pulse, and ring or oscillate during the pulse. It is most efficient that the electrical energy be delivered to the electrodes comprising the subsonic pressure wave generator(s) while the balloon fluid F comprises a mass density that is relatively high, roughly in the first 1-20 usec.

The current and voltage output may be monitored for proper operation. Measuring opens or shorts may produce a prompt or alert to change a catheter assembly for a new catheter assembly. Monitoring the DC impedance between the electrodes, e.g., 201 and 202, and the patient allows catheter insulation leaks to be sensed and corrected. As further described herein, monitoring the DC resistance between the electrodes may provide a temperature monitor. Still further, if the vessel is successfully being opened by treatment, the DC resistance between the electrodes decreases because of the larger cross section of saline conducting between the electrodes. It is further understood that as gas is produced from the arcs, the resistance will change.

Further, sensing and/or monitoring the conductivity of the conducting fluid F within the balloon alone, or comparing same with the conductivity of fluid, e.g., blood, outside of the balloon provides alternative mechanisms for determining whether the balloon has been compromised, e.g., a rupture or tear.

The patient's heart rhythm may be monitored, and that these pulses are synchronized to an inactive phase. That synchronization precludes some standard methods, such as a spark gap that closes when the capacitor bank reaches a target voltage. Relatedly, the balloon 104 will expand and contract with a characteristic time and frequency. Voltage pulses may be timed to take advantage of the natural expansion/contraction cycle and frequency. For example, voltage pulses may be timed to the natural expansion of the balloon and/or to the natural contraction of the balloon. The force of the subsonic pressure waves will impact the target tissue and/or occluding material, e.g., calcification, at slightly different angles depending on the balloon's expansion state, because, inter alia, the subsonic pressure wave generators position will change with expansion/contraction of the balloon.

Temperature Sensor

As discussed above, certain embodiments may comprise a small temperature sensor embedded near the electrodes and/or within the conductive fluid F which may increase the treatment pulse rate up to the limit of a safe rise in tissue temperature—generally local tissue temperature should not be increased more than about 1 degree C. Heat diffusion on the order of 5 mm from the electrodes is required for the heat to be convected by blood circulation. The thermal diffusion time for water at in conduits of relevant radius range is (5 mm)2/k=167 seconds. However, a 0.5 J pulse raises a 5 mm radius sphere of water approximately 0.23 degrees C., so a 1-pulse/spark-per-minute rate may be increased to 2-pulses/sparks-per minute in certain embodiments.

The temperature sensor may be optical fiber based, or a micro-thermocouple. Since saline increases conductivity with temperature, the current produced by a DC bias applied to the electrodes will increase monotonically with temperature, allowing the temperature of the warmest region to be measured directly. As described above, a predetermined heat or temperature increase threshold may be provided with subsequent alerts and/or corrective or remedial actions implemented by programmed instructions implemented by a processor.

Balloon and Inflation Liquid

Angioplasty balloons are developed and nuanced. Embodiments of the present invention comprise standard angioplasty balloons and related, and known, basic inflation/deflation mechanisms. A typical balloon length may be 12 mm and may be used with 0.14-0.35 in guide wires. The inflated balloon size may comprise about 90% of the nominal vessel size.

Varying the salinity of the water used to inflate the balloon has an impact on the breakdown voltage between the electrodes similar to their spacing. Thus, electrode spacing to form a subsonic pressure wave generator may be selected to be appropriate for standard saline, or when a lower-than-saline salt concentration used to inflate the balloon, the electrode spacing may be increased past that used for standard saline. The current density prior to arc formation may be 50 A through 0.1 $cm^2$, or about 500 $A/cm^2$ at 2,000V, so an initial saline concentration should be at least 2.0 E-4 M NaCl. Standard saline is 0.9% NaCl, or 1.5 E-1 M, approximately 1000× more concentrated than required to initiate an arc.

The voltage pulse generated by the pulse generator 300 generates streamers in the fluid F interposed between, e.g., the proximal ring electrode 201 and the next more distal ring electrode 202 that comprise a subsonic pressure wave generator 200. As described above, the distal-most ring electrode is also operatively connected with the pulse generator 300. Sufficient voltage applied to the proximal ring electrode 201 results in streamers and ultimately current flowing between the two ring electrodes of the electrode pair 201, 202, generating an arc and a resultant subsonic pressure wave as a bubble forms and expands in the fluid F, and another subsonic pressure wave as the bubble collapses. Generally, the expansion time for the bubble expansion may be measured in terms of microseconds, e.g., approximately 30 microseconds. This expansion time is slow compared to the transit time of sound across the bubble. "Shock waves" require generation of pressure waves that travel at or greater than the speed of sound.

We note here that this relatively slow expansion time, inter alia, ensures that the pressure wave generated is subsonic. In contrast, an actual shock wave, i.e., traveling at or greater than the speed of sound, is generated with a much shorter voltage pulse, on the order of tens of nanoseconds.

The distance between ring electrodes of an electrode pair, e.g., 201, 202 may be relatively long, e.g., 5 mm or longer. In this case, the generated bubble and resulting pressure wave may comprise cylindrical shapes, with the end portions of each more spherical in shape.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

Having described the invention, we claim:

1. A pressure wave generating catheter system comprising:
- a catheter;
- a plurality of electrodes disposed within in the catheter;
- a fluid-fillable balloon enclosing the plurality of electrodes;
- a pulse generator in electrical communication with the plurality of electrodes in the catheter, wherein the pulse generator is configured to:
  - for a given cycle, cause a first voltage pulse to be applied to at least a portion of the plurality of electrodes in the catheter, after which a second voltage pulse is applied to at least a portion of the plurality of electrodes in the catheter, the first voltage pulse causing an initial pressure wave, and wherein the second voltage pulse occurs prior to the initial pressure wave resulting from the first voltage pulse dissipating;

a processor coupled to the pulse generator, the processor executing pre-programmed instructions comprising various timing sequences of pulses and delays resulting in a plurality of arcs that cause pressure waves to occur together but with at least one pressure wave delayed from another pressure wave.

2. The pressure wave generating catheter system of claim 1, wherein the second voltage pulse, in combination with the first voltage pulse, causes a combined pressure wave.

3. The pressure wave generating catheter system of claim 2, wherein each of the first voltage pulse and the second voltage pulse causes its own pressure wave, which combine to form the combined pressure wave.

4. The pressure wave generating catheter system of claim 1, wherein the second voltage pulse causes a change in the initial pressure wave.

5. The pressure wave generating catheter system of claim 1, wherein the first voltage pulse and the second voltage pulse have different magnitudes.

6. The pressure wave generating catheter system of claim 1, wherein the first voltage pulse and the second voltage pulse have different time durations.

7. A method of generating pressure waves within a fluid-filled balloon of a catheter system, the method comprising:

inserting a catheter having a plurality of electrodes into a vessel;

filling a balloon enclosing the plurality of electrodes with a fluid; and operating a pulse generator in electrical communication with the plurality of electrodes to:

for a given cycle, apply a first voltage pulse to at least a portion of the plurality of electrodes in the catheter, after which a second voltage pulse is applied to at least a portion of the plurality of electrodes in the catheter, wherein the first voltage pulse causes an initial pressure wave in the fluid, and the second voltage pulse occurs prior to the initial pressure wave resulting from the first voltage pulse dissipating.

8. The method of claim 7, further comprising executing, by a processor coupled to the pulse generator, pre-programmed instructions including a plurality of timing sequences of pulses and delays resulting in a plurality of arcs that cause pressure waves to occur together with at least one pressure wave delayed from another pressure wave.

9. The method of claim 7, wherein the second voltage pulse, in combination with the first voltage pulse, produces a combined pressure wave.

10. The method of claim 9, wherein each of the first voltage pulse and the second voltage pulse produces its own pressure wave, and the two pressure waves combine to form the combined pressure wave.

11. The method of claim 7, wherein the second voltage pulse alters or modifies the initial pressure wave.

12. The method of claim 7, wherein the first voltage pulse and the second voltage pulse have different magnitudes.

13. The method of claim 7, wherein the first voltage pulse and the second voltage pulse have different time durations.

14. A pressure wave generating system comprising:

a catheter having a plurality of electrodes;

a fluid-fillable balloon enclosing the plurality of electrodes;

a pulse generator in electrical communication with the plurality of electrodes; and a processor coupled to the pulse generator, the processor executing computer-executable instructions that cause the pulse generator to:

for a given cycle, cause a first voltage pulse to be applied to at least a portion of the plurality of electrodes in the catheter, after which a second voltage pulse is applied to at least a portion of the plurality of electrodes in the catheter, the first voltage pulse causing an initial pressure wave, and wherein the second voltage pulse occurs prior to the initial pressure wave resulting from the first voltage pulse dissipating.

15. The pressure wave generating system of claim 14, wherein the second voltage pulse, in combination with the first voltage pulse, causes a combined pressure wave.

16. The pressure wave generating system of claim 15, wherein each of the first voltage pulse and the second voltage pulse causes its own pressure wave, which combine to form the combined pressure wave.

17. The pressure wave generating system of claim 14, wherein the second voltage pulse causes a change in the initial pressure wave.

18. The pressure wave generating system of claim 14, wherein the processor executes computer-executable instructions that cause the pulse generator to generate the first voltage pulse and the second voltage pulse to have different magnitudes.

* * * * *